(12) United States Patent
Borders et al.

(10) Patent No.: US 7,010,369 B2
(45) Date of Patent: Mar. 7, 2006

(54) MEDICAL EQUIPMENT CONTROLLER

(75) Inventors: Richard L. Borders, Erie, CO (US); Timothy D. Wildman, Metamora, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 2 days.

(21) Appl. No.: 10/430,643

(22) Filed: May 6, 2003

(65) Prior Publication Data

US 2003/0195644 A1 Oct. 16, 2003

Related U.S. Application Data

(60) Continuation-in-part of application No. 10/083,197, filed on Feb. 26, 2002, now Pat. No. 6,560,492, which is a division of application No. 09/187,825, filed on Nov. 6, 1998, now Pat. No. 6,351,678.

(60) Provisional application No. 60/064,709, filed on Nov. 7, 1997.

(51) Int. Cl.
*G06F 19/00* (2006.01)
(52) U.S. Cl. .................. 700/90; 340/539.1; 455/404.2
(58) Field of Classification Search ............... 710/83, 710/17, 223, 204, 15; 5/613, 600, 652, 616; 340/539.1–539.21, 425.5, 438, 439; 455/404.2; 700/90
See application file for complete search history.

(56) References Cited

U.S. PATENT DOCUMENTS

| | | |
|---|---|---|
| 3,439,320 A | 4/1969 | Ward |
| 3,739,329 A | 6/1973 | Lester |
| 4,151,407 A | 4/1979 | McBride et al. |
| 4,211,998 A | 7/1980 | Junginger et al. |
| 4,216,462 A | 8/1980 | McGrath et al. |
| 4,225,953 A | 9/1980 | Simon et al. |
| 4,231,019 A | 10/1980 | Junginger et al. |
| 4,244,596 A | 1/1981 | Chung |
| 4,275,385 A | 6/1981 | White |
| 4,435,862 A | 3/1984 | King et al. |
| 4,601,064 A | 7/1986 | Shipley |
| 4,649,385 A | 3/1987 | Aires et al. |
| 4,680,790 A | 7/1987 | Packard et al. |
| 4,712,105 A | 12/1987 | Kohler |
| 4,745,647 A | 5/1988 | Goodwin |
| 4,769,584 A | 9/1988 | Irigoyen et al. |
| 4,825,200 A | 4/1989 | Evans et al. |
| 4,837,568 A | 6/1989 | Snaper |
| 4,850,040 A | 7/1989 | Teich et al. |
| 4,871,997 A | 10/1989 | Adriaenssens et al. |
| 4,908,627 A | 3/1990 | Santos |
| 4,967,195 A | 10/1990 | Shipley |

(Continued)

FOREIGN PATENT DOCUMENTS

CH 675936 11/1990

(Continued)

OTHER PUBLICATIONS

"*TotalCare® Bed System Service Manual*", Hill-Rom®, A Hillenbrand Industry, pp. i through 1-2, pp. 1-32 through 1-41, and pp. 1-59 through 1-69, (48 pages).

(Continued)

*Primary Examiner*—Kidest Bahta
(74) *Attorney, Agent, or Firm*—Bose McKinney & Evans LLP

(57) ABSTRACT

A portable medical equipment controller apparatus including a user input device. A processor is configured to determine if a predetermined distance from a base unit is exceeded, and to signal an alert if the predetermined distance from the base unit is exceeded.

30 Claims, 23 Drawing Sheets

U.S. PATENT DOCUMENTS

| | | | |
|---|---|---|---|
| 4,990,892 A | 2/1991 | Guest et al. | |
| 4,999,622 A | 3/1991 | Amano et al. | |
| 5,016,172 A | 5/1991 | Dessertine | |
| 5,027,314 A | 6/1991 | Linwood et al. | |
| 5,051,741 A | 9/1991 | Wesby | |
| 5,062,151 A | 10/1991 | Shipley | |
| 5,072,463 A | 12/1991 | Willis | |
| 5,073,999 A | 12/1991 | Thomas et al. | |
| 5,119,104 A | 6/1992 | Heller | |
| 5,153,584 A | 10/1992 | Engira | |
| 5,199,118 A | 4/1993 | Cole et al. | |
| 5,202,666 A | 4/1993 | Knippscheer | |
| 5,218,344 A | 6/1993 | Ricketts | |
| 5,235,713 A | 8/1993 | Guthrie et al. | |
| 5,239,300 A | 8/1993 | Berger et al. | |
| 5,251,349 A | 10/1993 | Thomas et al. | |
| 5,289,163 A | 2/1994 | Perez et al. | |
| 5,309,144 A | 5/1994 | Lacombe et al. | |
| 5,317,303 A | 5/1994 | Ross et al. | |
| 5,317,309 A | 5/1994 | Vercellotti et al. | |
| 5,319,363 A | 6/1994 | Welch et al. | |
| 5,363,425 A | 11/1994 | Mufti et al. | |
| 5,387,993 A | 2/1995 | Heller et al. | |
| 5,390,238 A | 2/1995 | Kirk et al. | |
| 5,396,224 A | 3/1995 | Dukes et al. | |
| 5,402,469 A | 3/1995 | Hopper et al. | |
| 5,410,326 A | 4/1995 | Goldstein | |
| 5,417,222 A | 5/1995 | Dempsey et al. | |
| 5,426,425 A | 6/1995 | Conrad et al. | |
| RE35,035 E | 9/1995 | Shipley | |
| D362,660 S | 9/1995 | Fromson | |
| D363,552 S | 10/1995 | Teo et al. | |
| 5,455,851 A | 10/1995 | Chaco et al. | |
| 5,458,123 A | 10/1995 | Unger | |
| 5,465,082 A | 11/1995 | Chaco | |
| 5,471,404 A | 11/1995 | Mazer | |
| 5,493,283 A | 2/1996 | Hopper et al. | |
| 5,509,154 A | 4/1996 | Shafer et al. | |
| 5,515,426 A | 5/1996 | Yacenda et al. | |
| 5,534,876 A | 7/1996 | Erickson et al. | |
| 5,541,585 A | 7/1996 | Duhame et al. | |
| 5,542,136 A | 8/1996 | Tappel | |
| 5,542,138 A * | 8/1996 | Williams et al. | 5/658 |
| 5,544,376 A | 8/1996 | Fromson | |
| 5,548,637 A | 8/1996 | Heller et al. | |
| 5,561,412 A | 10/1996 | Novak et al. | |
| 5,572,195 A | 11/1996 | Heller et al. | |
| 5,576,952 A | 11/1996 | Stutman et al. | |
| 5,588,009 A | 12/1996 | Will | |
| 5,589,821 A * | 12/1996 | Sallen et al. | 340/573.4 |
| 5,594,786 A | 1/1997 | Chaco et al. | |
| 5,600,214 A | 2/1997 | Fromson | |
| 5,610,589 A | 3/1997 | Evans et al. | |
| 5,611,096 A | 3/1997 | Bartlett et al. | |
| 5,614,886 A | 3/1997 | Snell et al. | |
| 5,627,524 A | 5/1997 | Fredrickson et al. | |
| 5,627,584 A * | 5/1997 | Nishikori et al. | 348/72 |
| 5,633,742 A | 5/1997 | Shipley | |
| 5,650,769 A | 7/1997 | Campana, Jr. | |
| 5,650,770 A * | 7/1997 | Schlager et al. | 340/573.1 |
| 5,652,484 A | 7/1997 | Shafer et al. | |
| D382,543 S | 8/1997 | Tsung | |
| D382,645 S | 8/1997 | Bergeron | |
| 5,664,270 A | 9/1997 | Bell et al. | |
| 5,670,945 A | 9/1997 | Applonie | |
| 5,678,568 A | 10/1997 | Uckikubo et al. | |
| 5,689,229 A | 11/1997 | Chaco et al. | |
| 5,699,038 A | 12/1997 | Ulrich et al. | |
| 5,719,555 A * | 2/1998 | Zeytoonjian et al. | 340/571 |
| 5,722,059 A | 2/1998 | Campana, Jr. | |
| 5,742,233 A | 4/1998 | Hoffman et al. | |
| 5,745,272 A | 4/1998 | Shipley | |
| 5,754,997 A | 5/1998 | Lussi et al. | |
| 5,759,149 A | 6/1998 | Goldberg et al. | |
| 5,771,511 A | 6/1998 | Kummer et al. | |
| 5,774,865 A | 6/1998 | Glynn | |
| 5,781,942 A | 7/1998 | Allen et al. | |
| 5,787,528 A | 8/1998 | Antinori | |
| 5,796,338 A * | 8/1998 | Mardirossian | 340/571 |
| 5,812,059 A | 9/1998 | Shaw et al. | |
| 5,815,864 A | 10/1998 | Sloop | |
| 5,815,865 A * | 10/1998 | Washburn et al. | 5/713 |
| 5,818,617 A | 10/1998 | Shipley | |
| 5,822,418 A | 10/1998 | Yacenda et al. | |
| 5,822,544 A | 10/1998 | Chaco et al. | |
| 5,835,013 A | 11/1998 | Duterte | |
| 5,838,223 A | 11/1998 | Gallant et al. | |
| 5,874,896 A | 2/1999 | Lowe et al. | |
| 5,900,801 A | 5/1999 | Heagle et al. | |
| 5,901,172 A | 5/1999 | Fontana et al. | |
| 5,939,974 A | 8/1999 | Heagle et al. | |
| 5,939,988 A | 8/1999 | Neyhart | |
| 5,945,910 A | 8/1999 | Gorra | |
| 5,952,924 A | 9/1999 | Evans et al. | |
| 5,966,763 A | 10/1999 | Thomas | |
| 5,983,429 A | 11/1999 | Stacy et al. | |
| 6,009,333 A | 12/1999 | Chaco | |
| 6,026,125 A | 2/2000 | Larrick, Jr. et al. | |
| 6,038,718 A | 3/2000 | Penninig et al. | |
| 6,054,950 A | 4/2000 | Fontana | |
| 6,073,284 A | 6/2000 | Borders | |
| 6,084,517 A | 7/2000 | Rabanne et al. | |
| 6,111,508 A | 8/2000 | Ensor et al. | |
| 6,117,076 A | 9/2000 | Cassidy | |
| 6,125,482 A | 10/2000 | Foster | |
| 6,131,868 A | 10/2000 | Welling et al. | |
| 6,133,837 A | 10/2000 | Riley | |
| 6,135,949 A | 10/2000 | Russo et al. | |
| 6,147,592 A | 11/2000 | Ulrich et al. | |
| 6,149,674 A | 11/2000 | Borders | |
| 6,163,903 A | 12/2000 | Weismiller et al. | |
| 6,202,230 B1 | 3/2001 | Borders | |
| 6,211,790 B1 | 4/2001 | Radomsky et al. | |
| 6,236,317 B1 | 5/2001 | Cohen et al. | |
| 6,239,741 B1 | 5/2001 | Fontana et al. | |
| 6,252,512 B1 | 6/2001 | Riley | |
| 6,259,355 B1 | 7/2001 | Chaco et al. | |
| 6,262,660 B1 | 7/2001 | Segale et al. | |
| 6,265,974 B1 | 7/2001 | D'Angelo et al. | |
| 6,292,698 B1 * | 9/2001 | Duffin et al. | 607/32 |
| 6,304,186 B1 | 10/2001 | Rabanne et al. | |
| 6,336,235 B1 | 1/2002 | Ruehl | |
| 6,339,378 B1 | 1/2002 | Seidel | |
| 6,344,794 B1 | 2/2002 | Ulrich et al. | |
| 6,351,678 B1 | 2/2002 | Borders | |
| 6,353,950 B1 | 3/2002 | Bartlett et al. | |
| 6,367,020 B1 | 4/2002 | Klein | |
| 6,392,547 B1 | 5/2002 | Stewart et al. | |
| 6,409,229 B1 | 6/2002 | Shea | |
| 6,462,656 B1 | 10/2002 | Ulrich et al. | |
| 2001/0038330 A1 | 11/2001 | Garcia | |
| 2002/0196150 A1 | 12/2002 | Wildman | |
| 2003/0030569 A1 | 2/2003 | Ulrich et al. | |

FOREIGN PATENT DOCUMENTS

| | | |
|---|---|---|
| DE | 299 05 840 | 3/1999 |
| DE | 199 03 079 | 8/2000 |
| EP | 0 316 643 | 5/1989 |
| EP | 0 348 726 | 1/1990 |
| EP | 0 373 912 | 6/1990 |
| EP | 0 455 852 | 11/1991 |
| EP | 0 488 552 | 6/1992 |
| EP | 0 543 763 | 11/1992 |

| | | |
|---|---|---|
| EP | 626635 | 11/1994 |
| EP | 0 788 984 | 8/1997 |
| EP | 0 899 215 | 3/1999 |
| FR | 2 705 952 | 4/1993 |
| FR | 2 753 183 | 9/1996 |
| GB | 2 193 359 | 2/1988 |
| GB | 2 230 365 | 10/1990 |
| GB | 2 265 038 | 9/1993 |
| GB | 2 356 482 | 5/2001 |
| JP | 5-95978 | 4/1993 |

OTHER PUBLICATIONS http://www.currentdirections.com/hardware/zebra/r140.html, Aug. 8, 2002.
http://www.rfidusa.com/rfid_ zebra-r140printer.html, Aug. 8, 2002.
http://www.rfidusa.com/rfid_introduction.html, Aug. 8, 2002.
http://rapidttp.com/transponder/presre37.html, Aug. 8, 2002.
"Great New Product: Infrared Locator," Teleconnect, Feb., 1986.
T.H. Ooi, "Low Cost RF Identification and Locating System," IEEE Trans. On Consumer Electronics, vol. 35 No. 4, Nov. 1989, pp. 831-839.
United Identifications Systems Corp., Infra-Com, 1989.
The Computer for the 21$^{st}$ Century, Mark Weiser, Scientific American, Sep. 1991.
Keeping Track of Alzheimer and Dementia Prone Patients Just Got Easier, Security Tag Systems, Inc., 1991.
Infant Monitoring System, Sekurmed.
Ultra-Wideband Precision Asset Location System, Robert J. Fontana and Steven J. Gunderson, reprinted from 2002, *IEEE Conference on Ultra Wideband Systems and Technologies*, May 2002, Baltimore, MD.

* cited by examiner

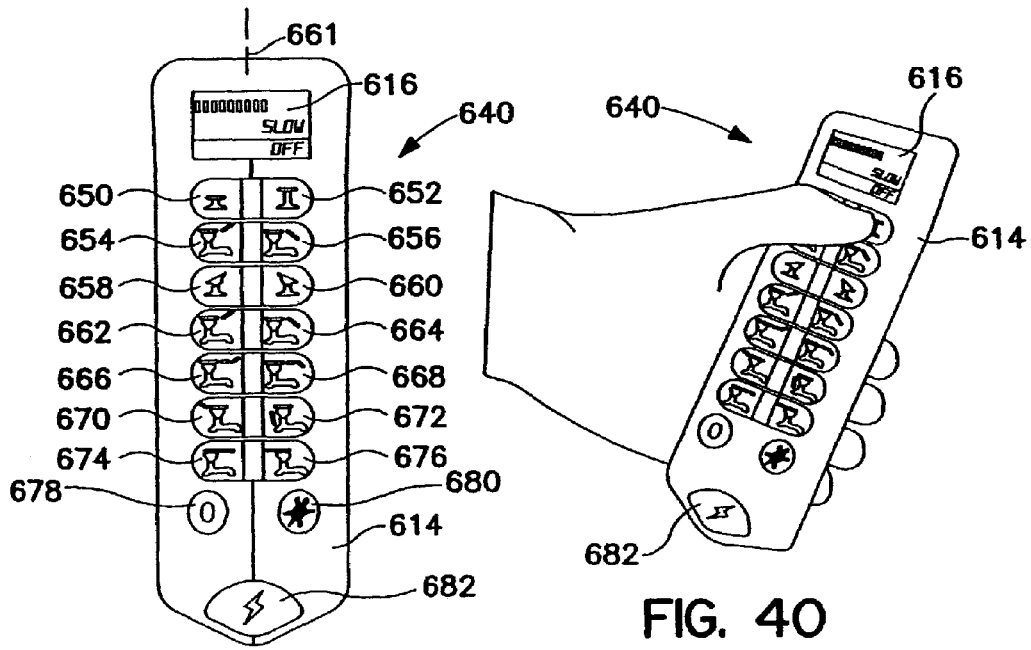
FIG. 39
FIG. 40
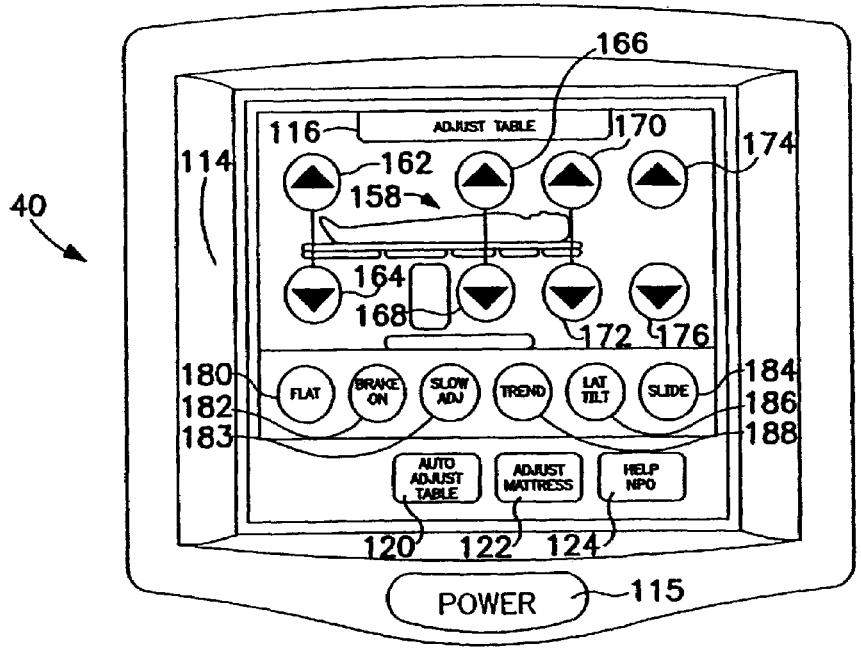
FIG. 13B

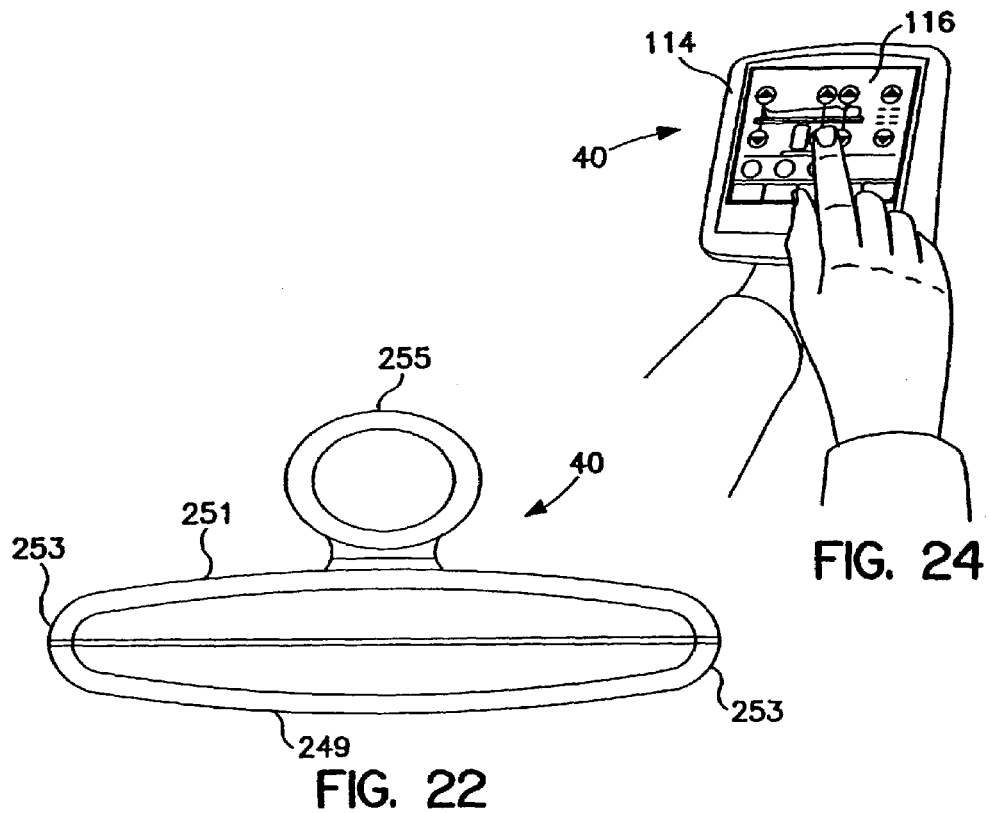
FIG. 24
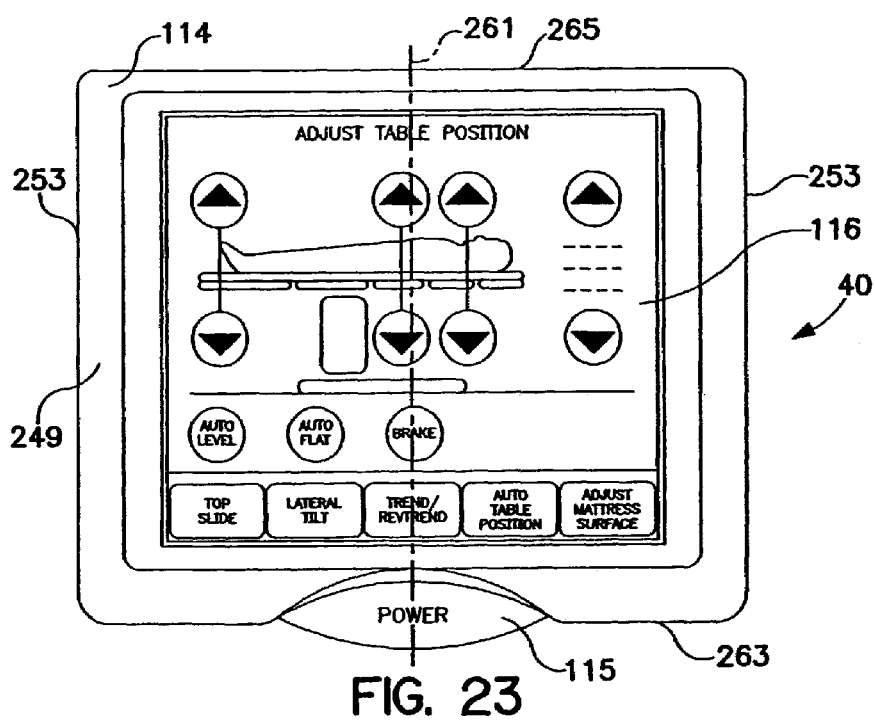
FIG. 22
FIG. 23

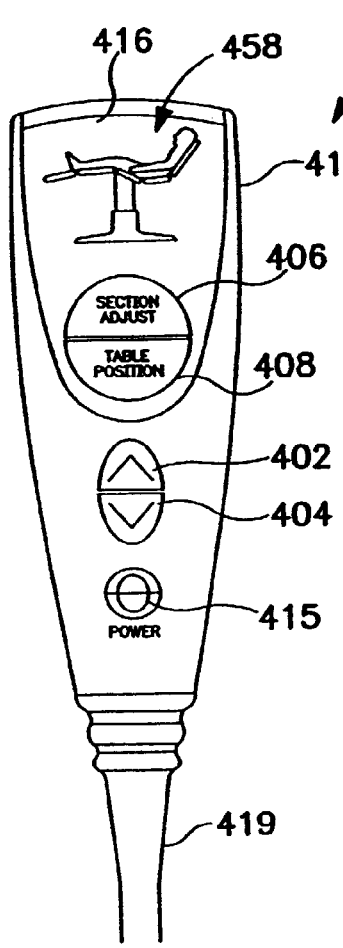
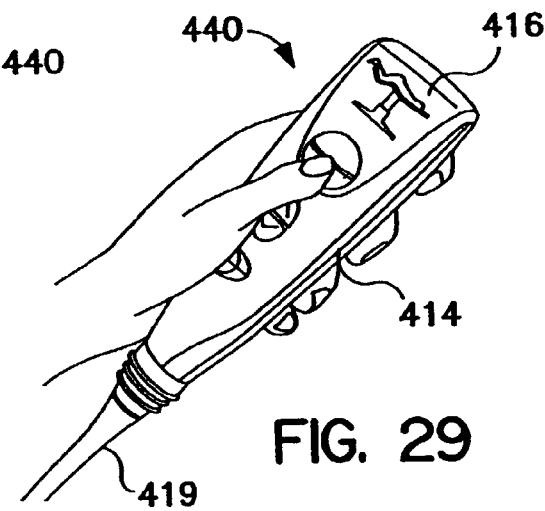
FIG. 29
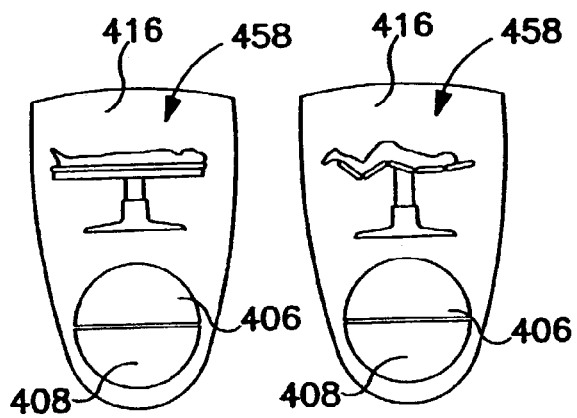
FIG. 30  FIG. 31
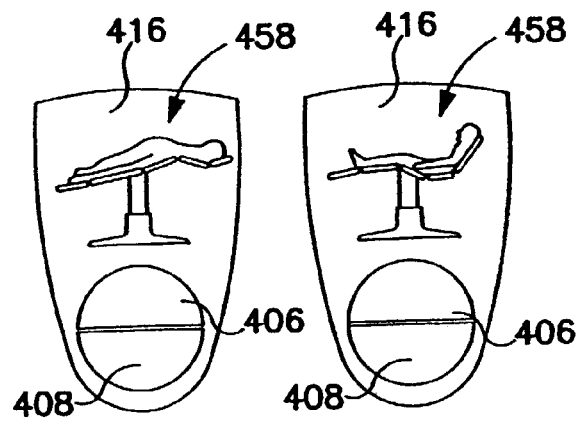
FIG. 32  FIG. 33
FIG. 28

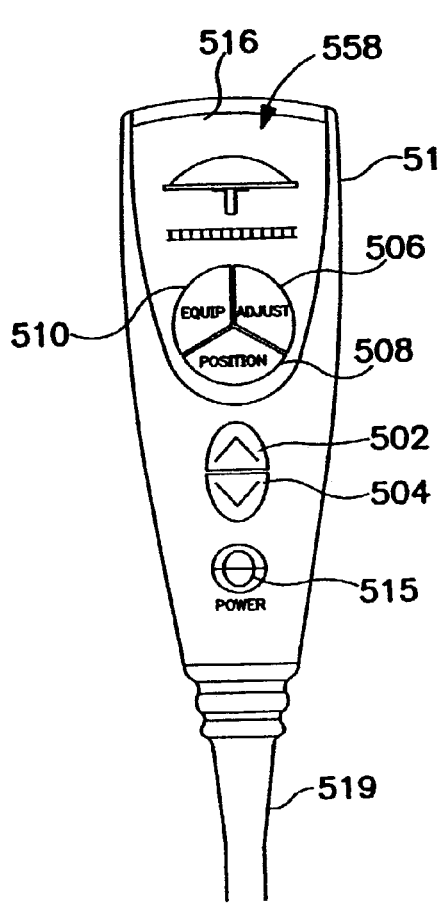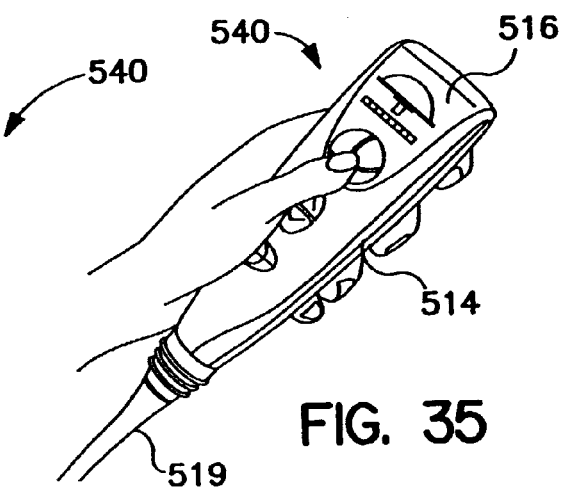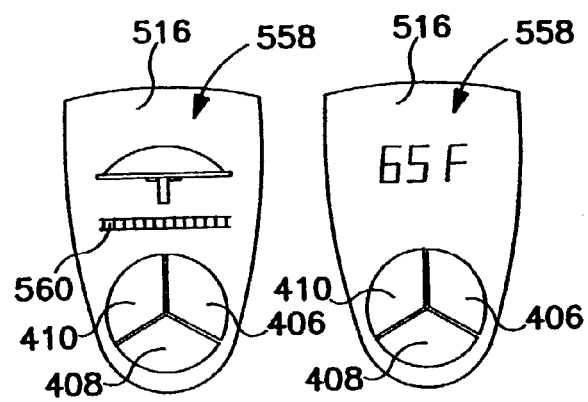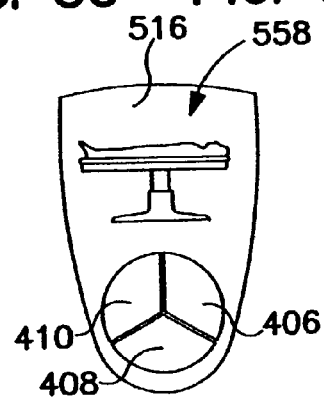
FIG. 34    FIG. 36    FIG. 37
FIG. 38

MEDICAL EQUIPMENT CONTROLLER

CROSS-REFERENCE TO RELATED APPLICATIONS

This application is a continuation-in-part of U.S. application Ser. No. 10/083,197, filed Feb. 26, 2002, now U.S. Pat. No. 6,560,492, which is a divisional of U.S. application Ser. No. 09/187,825, filed Nov. 6, 1998, now U.S. Pat. No. 6,351,678, which claims the benefit of U.S. provisional application Ser. No. 60/064,709, filed Nov. 7, 1997, the disclosures of which are expressly incorporated by reference herein.

BACKGROUND AND SUMMARY OF THE INVENTION

The present invention relates generally to device controllers, and particularly to device controllers for remote control of one or more pieces of medical equipment. More particularly, the present invention relates to medical device controllers for control of operating room equipment such as an articulated surgical table and a controllable mattress that is coupled to the articulated table.

Many medical devices are controllable, such as surgical tables with articulated support surfaces that use motors to adjust the support surfaces to desired configurations. Other examples include mattresses with multiple fluid chambers and systems for controlling fluid pressures within the chambers, or mattresses with vacuum beads for conforming the mattress surface to a patient. Similarly, surgical light systems are often controllable to vary the intensity and direction of a light source. A patient support system or treatment device can also include a controllable temperature subsystem, such as a resistive mattress cover, or a mechanism to control fluid temperature in a fluid-based mattress system, etc. Each controllable system typically includes its own separate control having multiple buttons, programming modes, and display configurations. An operator or care giver desiring to control each of these controllable systems must understand and operate the interface schemes for all of the associated controllers.

According to an illustrative embodiment of the present invention, a medical device controller apparatus includes a housing configured to be hand-held, a display coupled to the housing, and a user input device coupled to at least one of the display and the housing. The medical device controller apparatus further includes a processor coupled to the display, the processor being configured to command a controllable medical device, to determine if a predetermined distance from a base unit is exceeded, and to signal an alert if the predetermined distance from the base unit is exceeded.

Illustratively, the controllable medical device is a patient support apparatus comprising a base, a frame coupled to the base, the frame including a plurality of frame sections movable relative to each other to position the frame in a plurality of different frame configurations for a plurality of different medical procedures. The patient support apparatus further illustratively comprises a mattress located on the frame to support a patient, the mattress being adjustable to a plurality of different mattress configurations for the plurality of different medical procedures. The processor is configured to provide a menu on the display of a plurality of predefined configurations of the frame and mattress, the processor being configured to command the frame and the mattress to move to a selected one of the plurality of predefined configurations based on a user input.

Illustratively, the medical device controller apparatus further comprises a first transmitter and a first receiver both coupled to one of the base unit and the housing, a second transmitter and a second receiver both coupled to the other of the housing and the base unit. The first transmitter is configured to transmit a first signal to the second receiver, and the second transmitter is configured to transmit a second signal to the first receiver in response to the second receiver receiving the first signal. A processor is in communication with the first transmitter and the first receiver. The processor is configured to signal the alert when the time between the first transmitter transmitting the first signal and the first receiver receiving the second signal is greater than a predetermined value.

Further illustratively, the medical device controller apparatus comprises a transmitter coupled to one of the housing and the base unit, and a receiver coupled to the other of the base unit and the housing. The transmitter is configured to transmit a signal to the receiver, and a processor is configured to determine the strength of the signal received by the receiver and to signal the alert when the strength is below a predetermined value.

Further illustratively, the medical device controller apparatus comprises a transmitter coupled to one of the housing and the base unit, and a receiver coupled to the other of the base unit and the housing. The transmitter is configured to transmit a signal to the receiver, and a counter is configured to count successive time intervals between transmission of the signal from the transmitter and receipt of the signal by the receiver. A processor is configured to signal the alert when the count from the counter exceeds a predetermined value.

In a further illustrative embodiment, a medical device control system comprises a controllable medical device, a controller in communication with the controllable medical device and including a housing configured to be hand-held, and a user input device supported by the housing. One of a receiver and a transmitter is coupled to the housing, and the other of the transmitter and the receiver is located in a restricted zone. The transmitter is configured to transmit a signal for receipt by the receiver. A processor is in communication with the receiver and is configured to signal an alert when the signal is received by the receiver.

Illustratively, the other of the transmitter and the receiver establishes a perimeter defining the restricted zone. Further illustratively, the other of the transmitter and the receiver is positioned at a room exit.

In a further illustrative embodiment, a medical device control system comprises a controllable medical device, a controller in communication with the controllable medical device and including a housing configured to be hand-held, and a user input device supported by the housing. A first tag is coupled to the controllable medical device and is configured to transmit a first signal. A second tag is coupled to the housing and is configured to transmit a second signal. A monitor is configured to receive the first signal transmitted by the first tag and the second signal transmitted by the second tag. The processor is coupled to the housing and is configured to command the controllable medical device, to electronically link the first tag to the second tag, and to signal an alert when the monitor indicates that the first tag and the second tag are separated by a distance greater than a predetermined value.

Illustratively, the monitor comprises a plurality of detectors defining a plurality of different detection zones, and the processor is in communication with the plurality of detectors. The processor is configured to signal the alert when the first tag is detected within a first one of the detection zones and the second tag is detected within a second one of the detection zones.

Illustratively, the first tag comprises an RFID tag, the second tag comprises an RFID tag, and the monitor comprises an RFID detector.

Additional features of the invention will become apparent to those skilled in the art upon consideration of the following detailed description of the presently perceived best mode of carrying out the invention.

BRIEF DESCRIPTION OF THE DRAWINGS

The detailed description particularly refers to the accompanying figures in which:

FIG. 13B is a front elevation view of the medical device controller of FIG. 9, showing an adjust table screen somewhat similar to FIG. 13A, with Trendelenburg, lateral tilt, and slide selection indicators positioned adjacent auto flat, brake, and slow adjust input indicators, and automatic table adjustment, mattress adjustment, and help information selection indicators along the bottom of the display;

FIG. 22 is a top plan view of an embodiment of a medical device controller similar to the embodiment of FIGS. 9–11, showing a relatively slim housing profile that is symmetric about a longitudinal axis and a generally cylindrical handle appended to a central portion of a back surface of the housing to facilitate storage and ambidextrous use of the controller;

FIG. 23 is a front elevation view of the controller of FIG. 22 showing a power button and a display;

FIG. 24 is a perspective view of the controller of FIG. 22 showing a user holding the controller with one hand and entering commands on the touch-screen with the other hand;

FIG. 28 is a front elevation view of another embodiment of a medical device controller, showing a tapered housing with a graphical display, semi-circular adjust and select buttons, a pair of up/down buttons, and a recessed power button, each button aligned along a central vertical axis of the housing to facilitate ambidextrous use of the controller;

FIG. 29 is a perspective view of the controller of FIG. 28 showing left-handed use of the controller;

FIGS. 30–33 are front views of the display and the select and adjust buttons of the controller of FIG. 28, showing automatic configuration selection displays similar to the configurations of FIGS. 3–6;

FIG. 34 is a front elevation view of another embodiment of a medical device controller similar to that of FIG. 28, showing a tapered housing with a graphical display, three pie-shaped selection buttons, a pair of up/down buttons, and a recessed power button;

FIG. 35 is a perspective view of the controller of FIG. 24 showing left-handed use of the controller;

FIGS. 36–38 are front views of the display and selection buttons of the controller of FIG. 28, showing graphical interfaces for controlling a lighting system, a temperature control system, and a table;

FIG. 39 is a front elevation view of yet another embodiment of a medical device controller, showing a hand-held housing, a display, and several pairs of control buttons, each pair of buttons aligned along a central vertical axis of the housing to facilitate ambidextrous use of the controller;

FIG. 40 is a perspective view of the controller of FIG. 39 showing left-handed use of the controller;

DETAILED DESCRIPTION OF DRAWINGS

Figure 1:
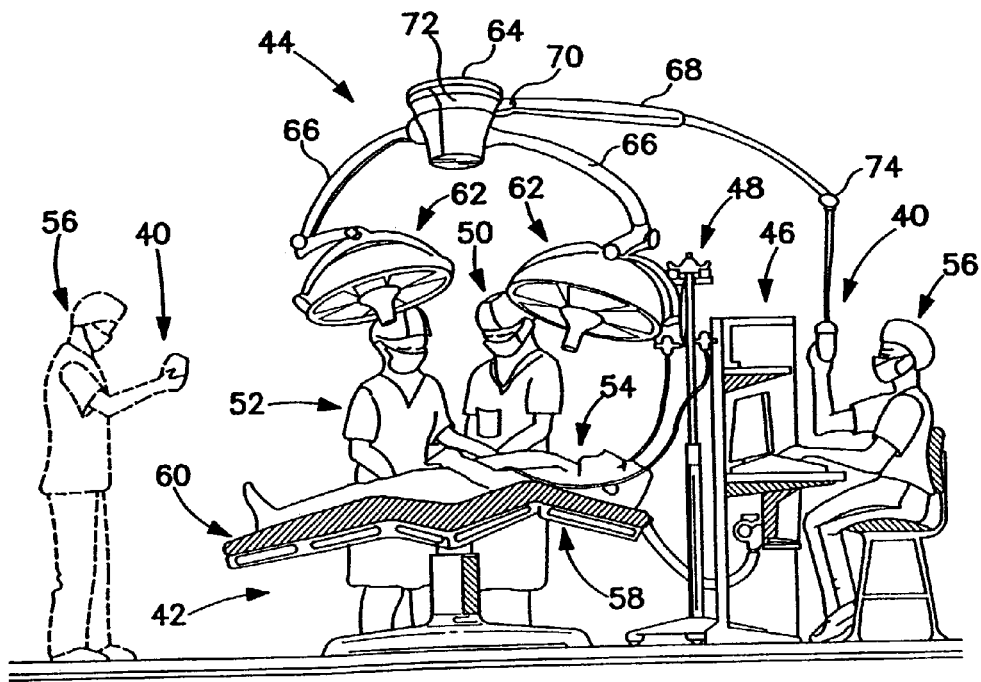
FIG. 1 is perspective view of an operating room environment showing a patient positioned atop a surgical table including an articulated frame and a mattress, a lighting system having a base unit and two light heads independently coupled to the base unit by articulated arms, an IV stand with a pair of IV bags coupled to the patient, a control station with a computer system interface to the surgical table, and a first medical device controller integrated with the operating room environment and coupled to the lighting system base unit by a telescoping and pivoting arm system and a second medical device controller shown with dashed lines integrated with the operating room environment and using a wireless communications link.

A medical device controller 40 according to the present invention is integrated into an operating room environment that includes a surgical table 42, a surgical lighting system 44, a control station 46, and an IV stand 48, as shown in FIG. 1. A surgeon 50 and one or more assistants 52 typically perform a procedure on a patient 54 while another care giver 56, such as an anesthesiologist or a nurse, controls and monitors operating room equipment from control station 46. Table 42 and lighting system 44 provide a variety of controllable features, as discussed in more detail below. Controller 40 provides a single, integrated, user-friendly interface for care giver 56 to control medical devices such as table 42 and lighting system 44.

Controller 40 is a hand-held device and can be configured to control medical devices through a variety of communication interfaces. For example, as shown in FIG. 1, lighting system 44 includes a base unit 64 coupled to light heads 62 via independent, articulated arms 66. Controller 40 can be coupled directly to based unit 64 by a telescoping arm 68. Telescoping arm 68 is coupled to base unit 64 by a horizontal pivot 70 and a vertical pivot 72, and includes a distal pivot 74, thereby providing for flexible movement of controller 40 throughout the operating room environment. In this configuration, signals between controller 40 and light heads 62 can be hard-wired through arms 66, 68 and base unit 64.

Controller 40 is either wired directly to the controllable devices or, preferably, is configured to send signals to the controllable devices using a wireless link, such as a radio frequency (RF), infrared (IR), or ultrasound communication link. Wireless communication links are well-known to those of ordinary skill in the art. Thus, it is within the scope of the present invention for controller 40 to use any means known to those skilled in the art to send signals to the controllable devices.

By using a wireless communication protocol, controller 40 is conveniently moved around the operating room environment by care giver 56, for example as shown by dashed lines in FIG. 1. A sterile sheath (not shown), made from a suitably flexible and transparent material such as thin latex rubber, is provide to encapsulate controller 40 so that it can be safely used throughout an operating room without contaminating the sterile environment. The sterile sheath may include a anti-microbial agent to further facilitate a sterile environment. By providing a single controller 40 that integrates controls for several operating room devices, and allowing controller 40 to be moved freely throughout the environment, the present invention increases operating room efficiency.

Figure 2:
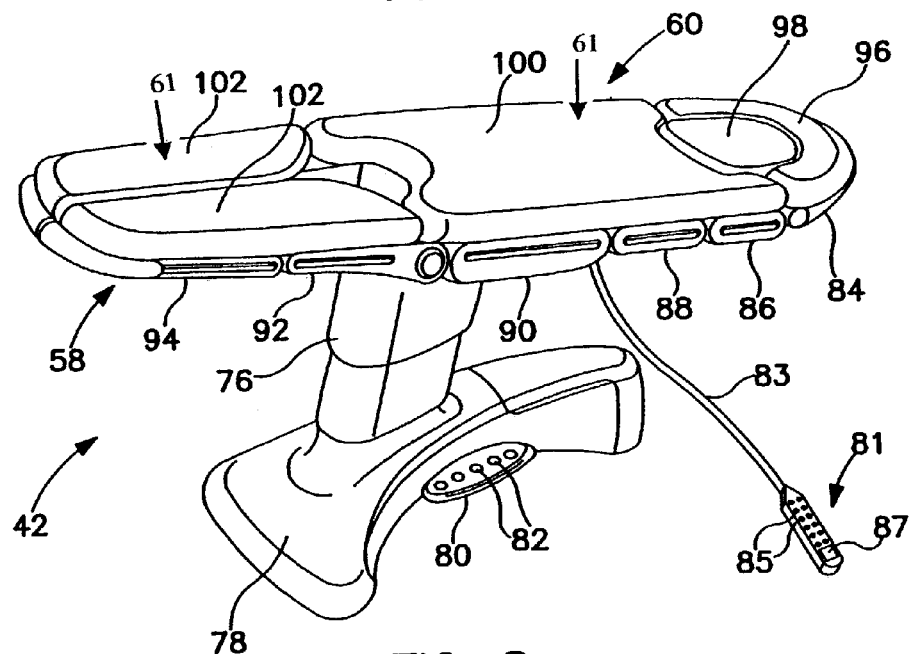
FIG. 2 is a perspective view of a controllable surgical table of the type shown in FIG. 1, including a base having foot controls, a vertically adjustable support column coupled to the base, an articulated frame coupled to the support column, a segmented mattress system supported by the articulated frame, and a pendant remote controller for controlling surgical table functions.
Figure 3:
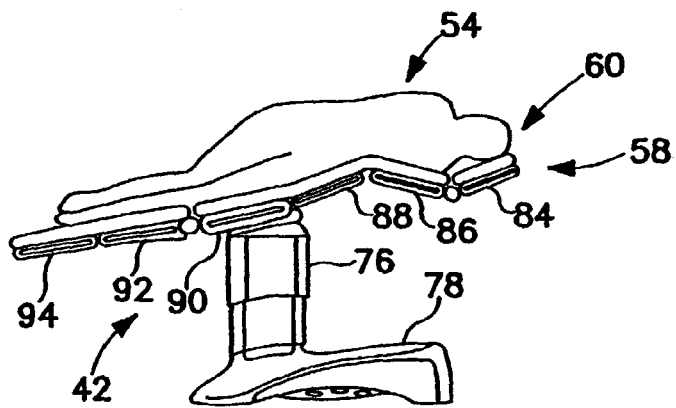
FIGS. 3–6 are side elevation views of the controllable surgical table of FIG. 2, showing the adjustable support column and articulated frame configured to support a patient in lateral, sitting, proctological, and lithotomy configurations for various medical or surgical procedures.
Figure 4:
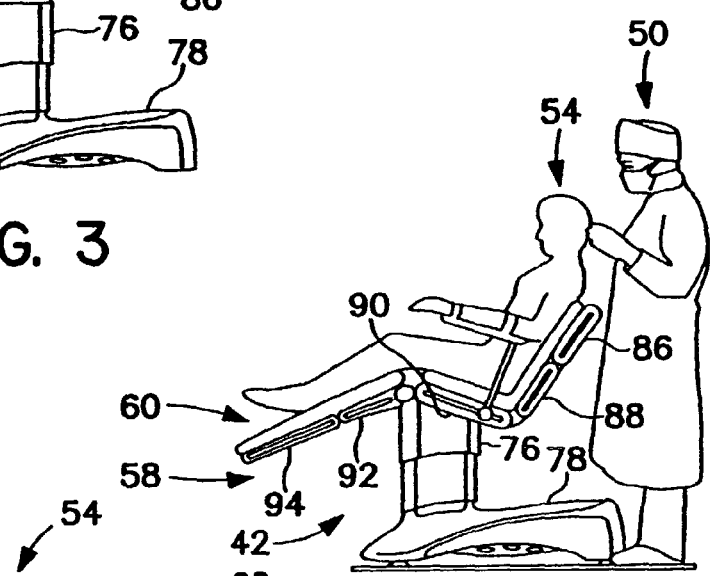
Figure 5:
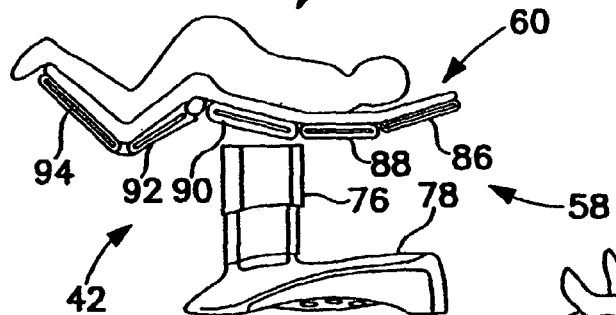
Figure 6:
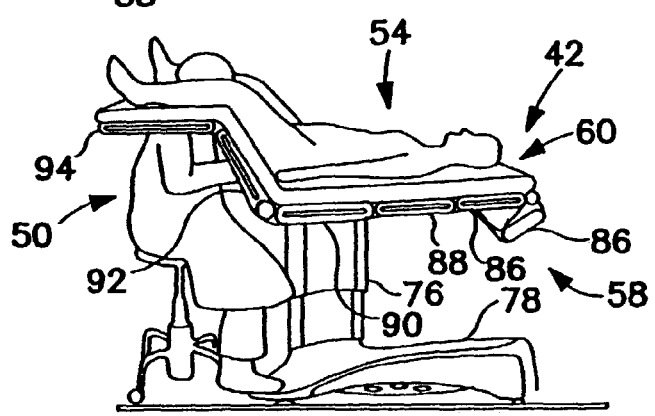

Modern surgical tables such as the illustrative table 42 shown in FIGS. 1–6 provide a variety of controllable functions. Table 42 includes articulated table frame 58, mattress 60, vertical support column 76, and base 78. Base 78 includes a foot control panel 80 having a plurality of control buttons 82, for adjusting vertical support column 76, mattress 60, and articulated table frame 58. As shown in FIG. 2, a pendant controller 81 coupled by a tether 83 to frame 58 similarly includes a plurality of control buttons 85 as well as a display 87. Pendant controller 81, which can be coupled to table 42 at any convenient location, similarly provides for adjusting frame 58, mattress 60, and support column 76.

Articulated table frame 58 includes a head section 84, an upper back section 86, a lower back section 88, a seat section 90, a pair of upper legs section 92, and a pair lower legs section 94. Sections of table frame 58 are coupled to longitudinally adjacent sections via pivots so that adjacent sections can be rotated with respect to each other by motors (not shown) or other suitable actuators well-known to those skilled in the art. Support column 76 is similarly vertically adjustable by a motor or actuator (not shown). Adjustment of articulated table frame sections 84, 86, 88, 90, 92, 94, and vertical support column 76 can be controlled by buttons 82 or, as discussed in more detail below, via controller 40.

Mattress 60 illustratively includes an outer head section 96, an inner head section 98, a torso section 100, and a pair of legs section 102. Torso section 100 and legs section 102 illustratively include a plurality of chambers 61 that are individually controllable. Mattress 60 can be any type of controllable mattress surface, e.g., some type of fluid mattress such as an air mattress, or a vacuum bead mattress, etc. In the context of the embodiments of the invention as discussed below, mattress 60 illustratively is a vacuum bead air mattress system in which mattress sections 96, 98, 100, and 102 can include multiple chambers and are coupled to a pressure and vacuum system to allow for selectively controlling the amount of pressure or vacuum in any chamber within any of the sections. Mattress 60 also includes a plurality of pressure sensors (not shown) to allow for measuring pressure within any chamber of the mattress sections. An illustrative controllable mattress is disclosed in U.S. Pat. No. 5,966,763, entitled "Surface Pad System for a Surgical Table", which is hereby incorporated by reference.

Surgical table 42 can be placed into configurations to support various medical or surgical procedures as shown, for example, in FIGS. 3–6. As discussed in more detail below, controller 40 provides for automatically placing table 42 in a desired, predefined configuration, such as those shown in FIGS. 3–6, as well as for incrementally adjusting table frame 58 and mattress 60 as required to accommodate variations needed for any particular doctor 50 or patient 54.

Features of controllable tables such as surgical table 42 are also discussed and shown in detail in U.S. Pat. Nos. 6,073,284; 6,149,674; and 6,202,230, all of which are hereby incorporated by reference.

Figure 7:
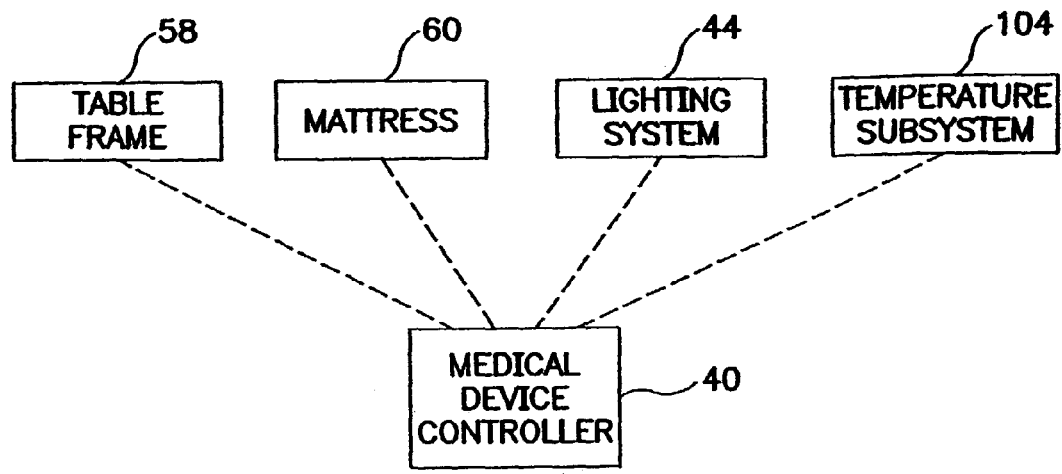
FIG. 7 is a block diagram showing interfaces between a medical device controller according to the present invention and a surgical table, mattress surface, heating subsystem, and lighting system.
Figure 8:
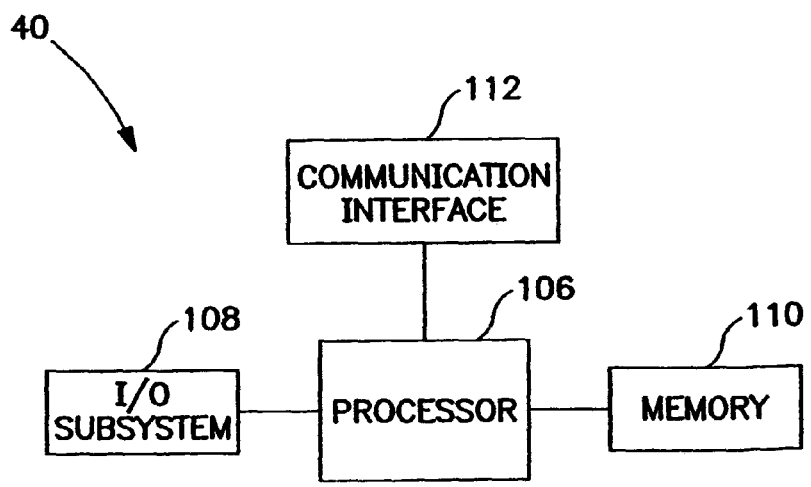
FIG. 8 is a block diagram showing an architecture of the medical device controller of FIG. 7, showing a processor coupled to display, user input, and device communication subsystems.

As illustrated by the block diagram of FIG. 7, controller 40 provides a single, mechanism for an operator, such as care giver 56, to control features of articulated frame 58 or mattress 60 of surgical table 42, as well as other controllable systems such as a lighting system 44 or a temperature control subsystem 104 that can be integrated with mattress 60. As shown in FIG. 8, a basic architecture for controller 40 can be a processor 106 that is coupled to an I/O subsystem 108, a memory 110, and a communication interface 112. Processor 106 is illustratively a microprocessor or a microcontroller (the latter can include integral memory to alleviate the need for a separate memory 110.) By providing a processor-based architecture with memory 110, controller 40 can be reconfigured or reprogrammed as needed to provide for control of new or different controlled medical devices, user interface needs, or external interface requirements. It is only necessary for a controlled device to be compatible with communication interface 112 as provided with controller 40.

Controller 40's I/O subsystem 108 is illustratively a touch-screen display system which provides a backlit, liquid crystal display 116. The touch screen input signals are illustratively provided by a matrix of translucent, membrane-type switches (not shown) positioned above display 116, although any touch-screen technology known to those skilled in the art can be used, such as those provided with personal digital assistant devices such as an Apple Newton™ or PalmPilot™ devices. Furthermore, although a touch-screen display is preferred for I/O subsystem 108, a display with buttons or switches arranged near the display screen is also contemplated.

Communication interface 112 illustratively is a pulsed infrared communication system, which technology is well known in the art. Table 42 is coupled to an IR receiver system (not shown) that provides for receiving IR signals from controller 40 for commanding frame 58 and mattress 60 based on received IR command signals. As discussed above, a hard-wired communication link can be used, or other wireless communication systems can be used, such as an RF-based system, or an ultrasound system, or any other type of wireless technology. Communication interface 112 can also be configured to support multiple communication protocols or interfaces, for example by including a hard-wired connection to support one controlled subsystem and an infrared connection to support other controlled subsystems.

Figure 9:
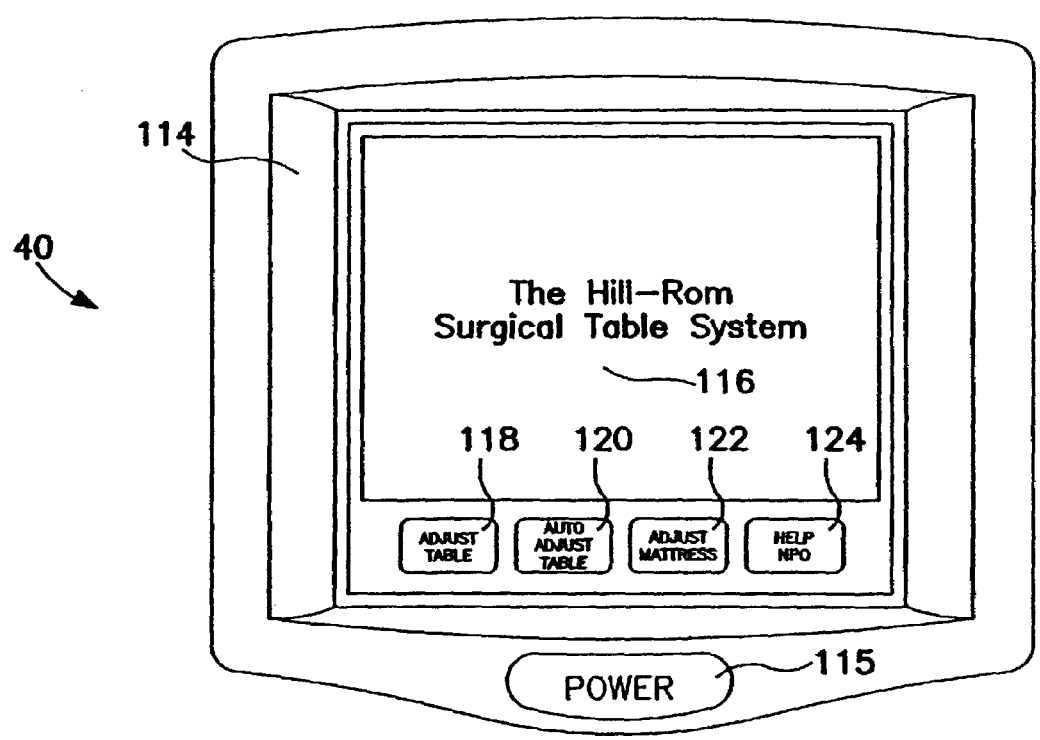
FIG. 9 is a front elevation view of a medical device controller according to the present invention showing a power button and a touch-screen display presenting an introductory menu with selection indicators for accessing controller functions to adjust a surgical table, to automatically adjust the table to predefined configurations, to adjust a mattress, or to obtain help from an on-line information guide.

Referring now to FIG. 9, controller 40 includes a housing 114, a power button 115, and a touch-screen display 116. Controller 40 is a hand-held unit that includes microprocessor or microcontroller 110 programmed to control a surgical table system such as that shown in FIGS. 1–6 via an IR or RF communication link 112 and to provide the user interface displays as shown in FIGS. 9–21. Controller 40 is powered on by depressing power button 115, whereupon the introductory display shown in FIG. 9 is provided, which includes four touch-screen selection indicators 118, 120, 122, 124 to designate to an operator access to further display interfaces for surgical table adjustment, automatic table adjustment, mattress adjustment, or accessing help information, respectively. Selection indicators 118, 120, 122, 124 are provided above touch-screen input switches included in touch-screen display 116 such as membrane switches (not shown), although, again, other touch-screen technologies can be used, or selection indicators 118, 120, 122, 124 can be positioned near buttons or switches provided along edges of display 116.

Figure 10:
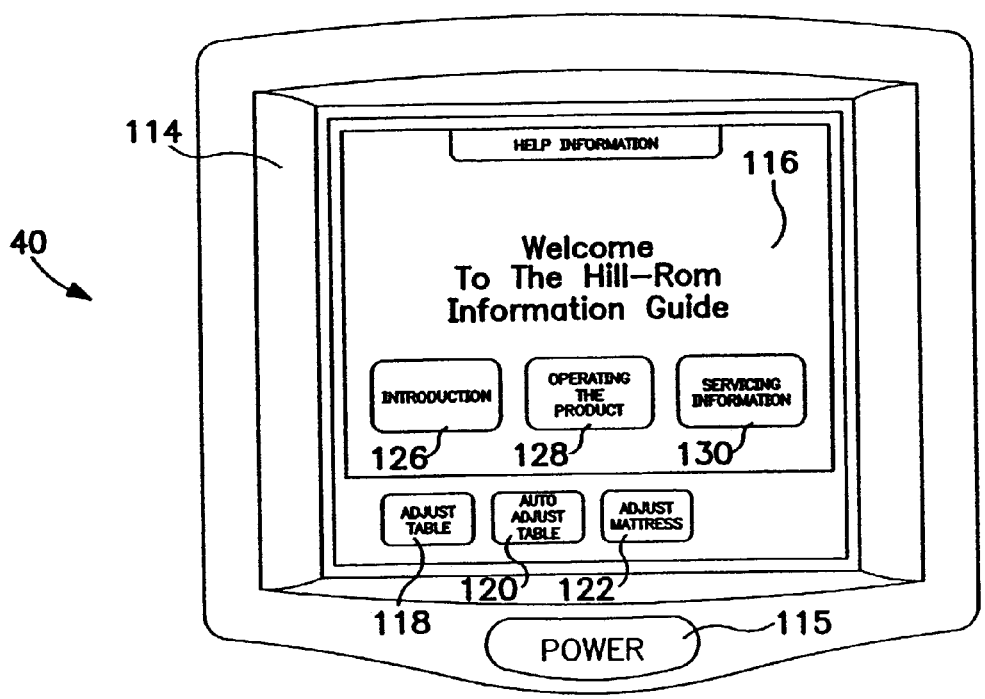
FIG. 10 is a front elevation view of the medical device controller of FIG. 9, showing a display accessed via the help selection, with selection indicators provided for obtaining introductory help information, operating instructions for controllable devices, and servicing information.

Controller 40 includes software programmed so that access of help information via selection indicator 124 from the display of FIG. 9 yields display of the help information screen of FIG. 10. Help information selection indicator 124 is removed, and more detailed help-related selection indicators 126, 128, 130 are provided for designating access to introduction, product operation, and servicing information screens. These detailed help screens provide on-line information that an operator otherwise would typically need to consult printed manuals to obtain.

Introduction screens accessed via selection indicator 126 provide information on the use and capabilities of controller 40, while product operation screens accessed via selection indicator 128 provide tutorial information on the use and capabilities of controlled systems such as table 42. Servicing information screens accessed via selection indicator 130 provide both manual and automated service and diagnostic facilities. Automated features include internal diagnostics of controller 40 and reporting of any diagnostic or service information available from controlled systems such as table 42. Controller 40 can provide "built-in-test" screens that will exercise controlled systems and either automatically verify proper operation or prompt an operator to perform a verification. Controller 40 can automatically recognize required servicing information from any controlled device capable of reporting such information, and provide recommendations to the operator accordingly. By providing menu-based, on-line information for aspects of controller 40's operation and servicing, as well as providing on-line information on controlled systems such as table 42, controller 40 provides care givers with an efficient, user-friendly, integrated interface.

Figure 11:
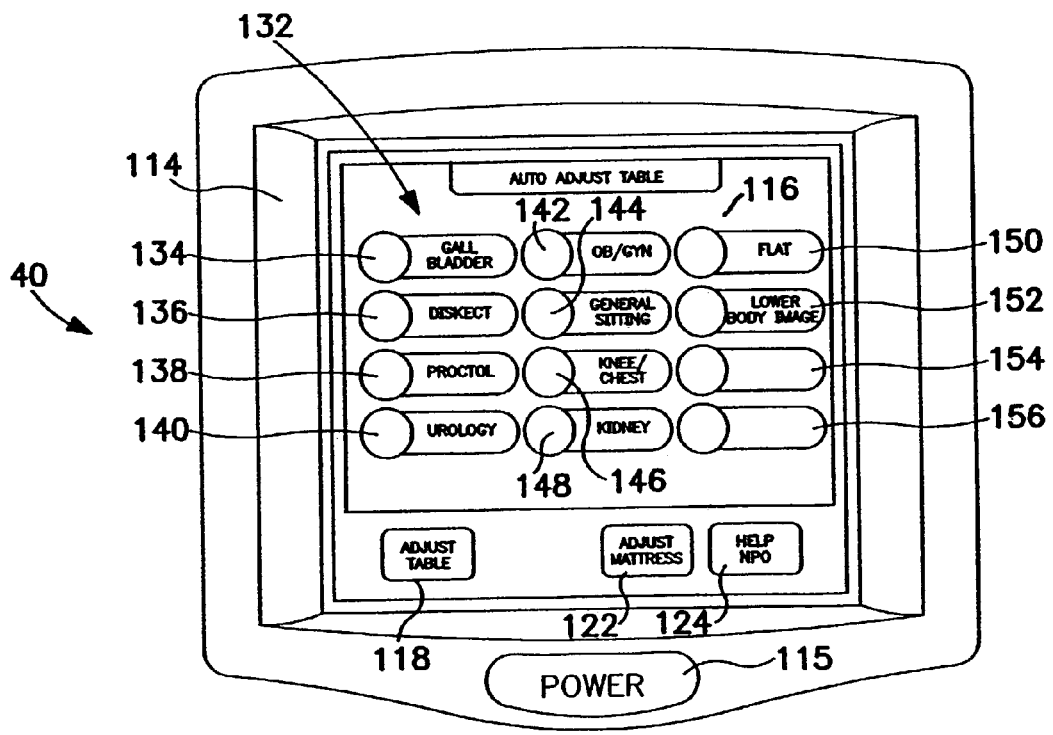
FIG. 11 is a front elevation view of the medical device controller of FIG. 9, showing a menu display accessed via the automatically adjust selection, with selection indicators provided for selecting table configurations described by surgical procedures.

Controller 40 includes software programmed so that selection via automatic table adjustment selection indicator 120 from the display of FIG. 9 yields display of an auto adjust table screen as shown in FIG. 11. Automatic table adjustment selection indicator 124 is removed and a descriptive menu 132 is provided for selecting various predefined configurations of surgical table 42. Menu 132 illustratively provides matrix of named table configurations 134 . . . 156, in which each configuration includes text descriptive of a surgical procedure or category placed next to a button symbol.

Figure 21:
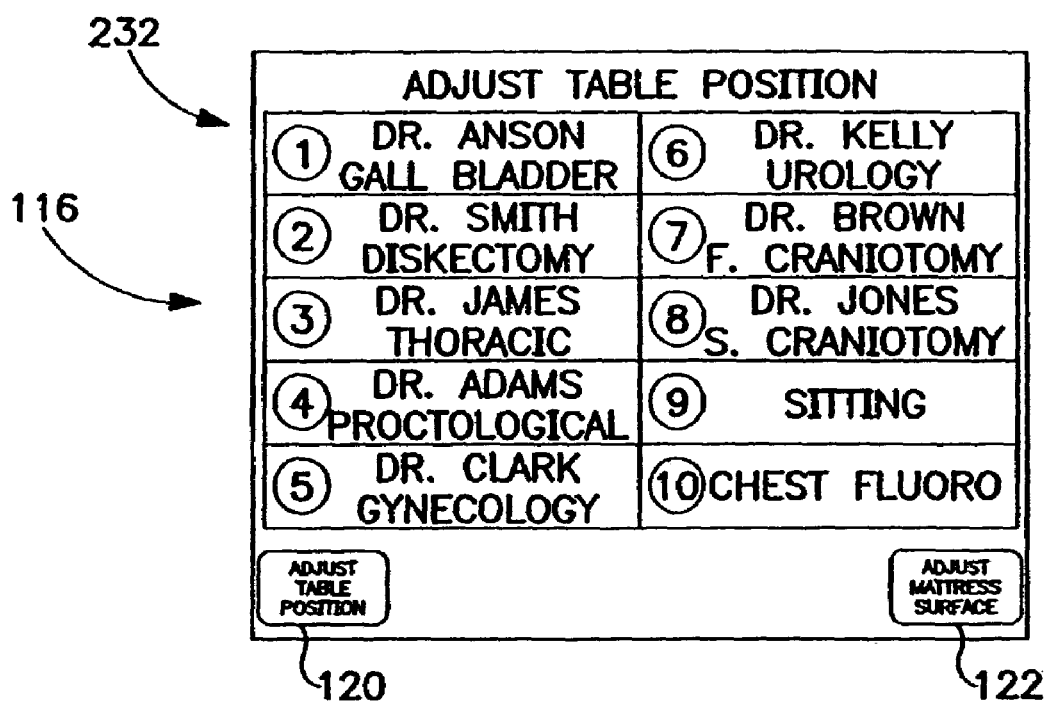
FIG. 21 is a front view of an alternative embodiment menu display similar to FIG. 11 with selection indicators provided for selecting predefined surgical table configurations described by doctor's names and/or surgical procedures.

An operator selects a configuration by pressing the adjacent button symbol, which is positioned on touch-screen display 116 above a touch-screen input switch. The descriptive text itself can be placed above one or more switches to achieve the same function by having the operator press directly above the text. The descriptive text can also be alternatively displayed near a button coupled to the housing along an edge of display 116. An alternative automatic table adjustment menu 232 is shown in FIG. 21, in which display 116 is partitioned into two columns each having five named table positions, with text that describes a medical or surgical configuration and in some cases an doctor's name. Although two columns of five named table positions are shown, the invention contemplates an arbitrary number of menu entries which can be presented on multiple screens or with a scrolling function. Alternative menu 232 illustrates how controller 40's display and processor-based architecture facilitates modifications of the user interface.

Figure 12:
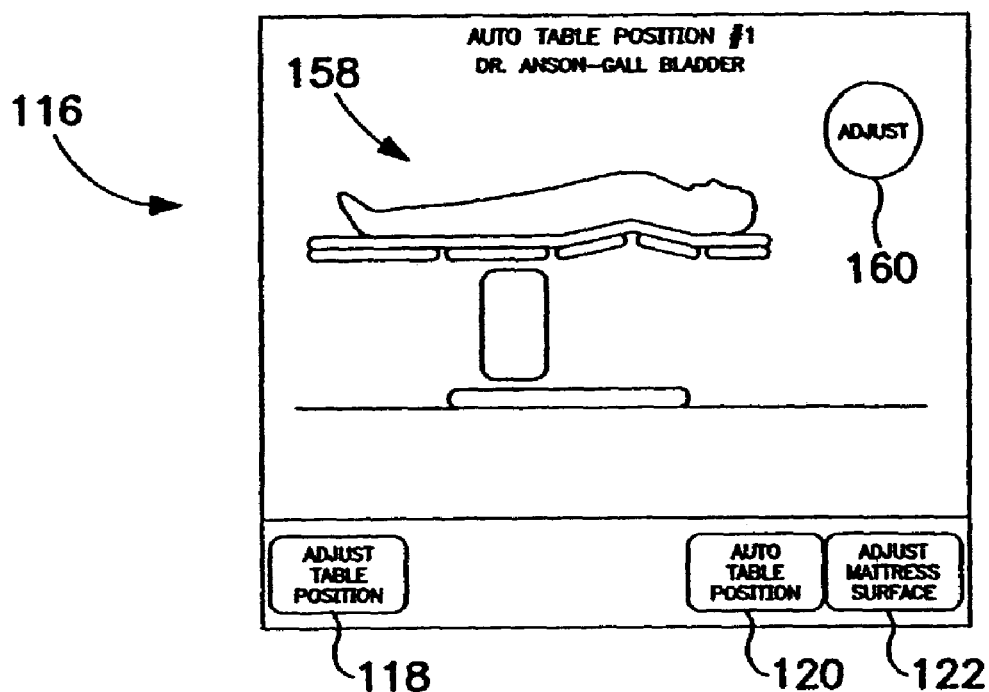
FIG. 12 is a front view of a display of a medical device controller similar to the display of FIGS. 9–11, showing an automatic configuration screen accessed from a menu selection such as provided by FIG. 11, the screen including an iconographic representation of a side view of a patient atop a mattress surface and articulated table frame configured consistently with the surgery description, and a selection indicator for an operator to automatically configure the table to the configuration corresponding to the iconographic representation.

Referring now to FIG. 12, a screen on display 116 based upon a selection of configuration 134, 234 from menu 132, 232 as shown in FIG. 11 or 21 is shown. An iconographic representation or pictogram 158 of a predetermined configuration of table 42 suitable for a gall bladder procedure, along with an adjust input indicator 160, are provided. Selection indicators 118, 120, 122 to designate access to table adjustment, automatic table adjustment, and mattress adjustment displays, respectively, are also provided.

Iconographic representation 158 provides a graphical depiction in outline form of table 42 as configured for a gall bladder procedure, including patient 54, mattress 60, sections 86, 88, 90, 92, 94 of articulated table frame 58, vertical support column 76, and base 78. If an operator wants to adjust table 42 automatically to the gall bladder configuration as depicted in iconographic representation 158, then the operator simply presses touch screen 116 above adjust input indicator 160. Software in controller 40 is configured to command table 42 to move to the predefined configuration only while a touch input is provided above adjust input indicator 160. This "press and hold" feature provides a safety interlock in that table 42 only moves while a positive user input is provided. This also allows an operator to select an intermediate configuration by terminating the touch input above adjust input indicator 160 before table 42 reaches the predefined configuration.

Figure 13A:
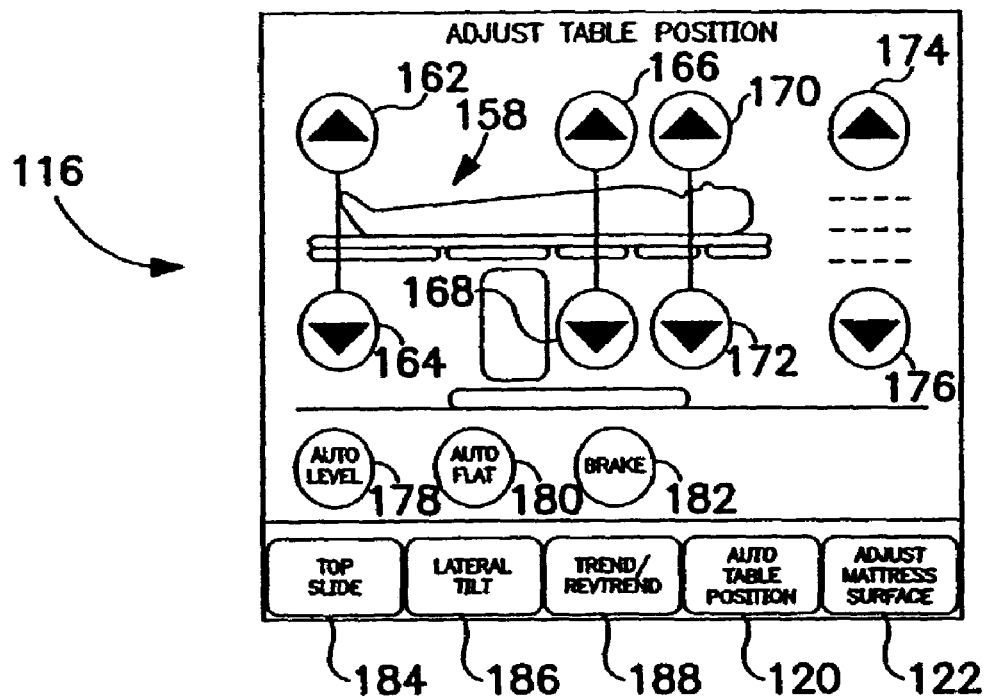
FIG. 13A is a front view of an adjust table position screen similar to FIG. 12, showing a table adjustment screen for adjusting a surgical table, including an iconographic representation of a patient atop a mattress surface and articulated table frame, with input indicators for adjusting articulated table frame sections and a vertically adjustable support column, input indicators for automatically leveling the table, automatically flattening the table surface, and engaging a floor brake, and selection indicators along the bottom of the display for accessing further adjustment screens.

Selection of the surgical table adjustment function, for example via selection indicator 118 as shown in FIGS. 9–12, results in the display of FIG. 13A. Iconographic representation 158 is provided with elements of table frame 58 and mattress 60 shown in nominal positions, along with up and down adjustment input indicators 162, 164, 166, 168, 170, 172, 174, 176, auto level input indicator 178, auto flat input indicator 180, and brake input indicator 182. Selection indicators 184, 186, 188 are provided along the bottom of display 116 for accessing top slide, lateral tilt, and Trendelenburg adjustment display screens, as are selection indicators 120, 122 for automatic table adjustment and mattress adjustment.

Up and down adjustment input indicators 162, 164, 166, 168, 170, 172, 174, 176 provide for "press and hold" adjustment of designated sections of articulated frame 58 as indicated by the graphical display and their placement relative to iconographic display 158. Up and down input indicators 162, 164 designate control of lower leg sections 94, indicators 166, 168 designate control of lower back section 88, indicators 170, 172 designate control of upper back section 86, and indicators 174, 176 designate control of vertical support column 76. Up and down adjustment of designated sections provides for fine tuning the configuration of frame 58 from any predefined configuration.

Auto level input indicator 178 provides for automatically moving all articulated sections of frame 58 to achieve a level (horizontal) configuration. Like adjust input indicator 160 discussed above, auto level input indicator 178 can be used to achieve intermediate configurations via the "press and hold" feature. Similarly, auto flat input indicator 180 provides for automatically moving all articulated sections of frame 58 to achieve a flat configuration (while maintaining any preexisting longitudinal inclination of frame 58 with respect to the ground). Brake input indicator 182 provides for locking or unlocking one or more wheels or casters (not shown) provided on base 78 of table 42 to prevent movement of table 42 along the ground.

An alternative table adjustment display somewhat similar to FIG. 13A is shown in FIG. 13B, with input indicators performing the same functions labeled with the same reference numbers. The table adjustment display of FIG. 13B displays only "high level" selection indicators 120, 122, 124 for automatic table adjustment, mattress adjustment, and help information along the bottom of display 116. Selection indicators 184, 186, 188 for table sliding, Trendelenburg tilting, and lateral tilting are displayed near auto flat 180, brake 182, and slow adjust 183 input indicators. FIG. 13B illustrates how controller 40's architecture permits reprogramming to provide a user interface as desired.

Figure 14:
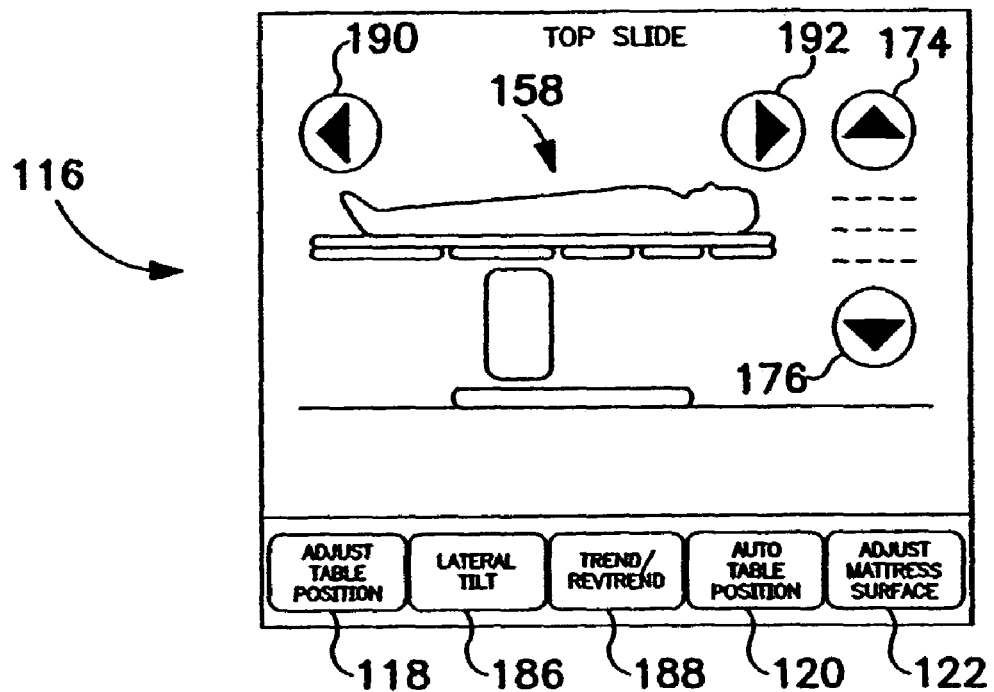
FIG. 14 is a front view of a top slide screen similar to FIG. 12, showing input indicators for sliding the table surface from end-to-end relative to the support column and for adjusting the vertical support column.

A top slide display accessible via selection indicator 184 is provided for moving table frame sections 84, 86, 88, 90, 92, 94 longitudinally relative to vertical support column 76 as shown in FIG. 14. Iconographic representation 158 is provided with frame 58 shown in a level configuration, although a representation showing a current configuration of articulated sections 84, 86, 88, 90, 92, 94 can be provided. Head end and foot end slide input indicators 190, 192 for sliding frame 58 longitudinally relative to vertical support column 76 provide "press and hold" capability as discussed above for the up and down input indicators of FIG. 13A. Vertical up and down input indicators 174, 176 are also provided on display 116, as are table adjustment, lateral tilt, Trendelenburg adjustment, automatic table adjustment, and mattress adjustment selection indicators 118, 186, 188, 120, 122.

Figure 15:
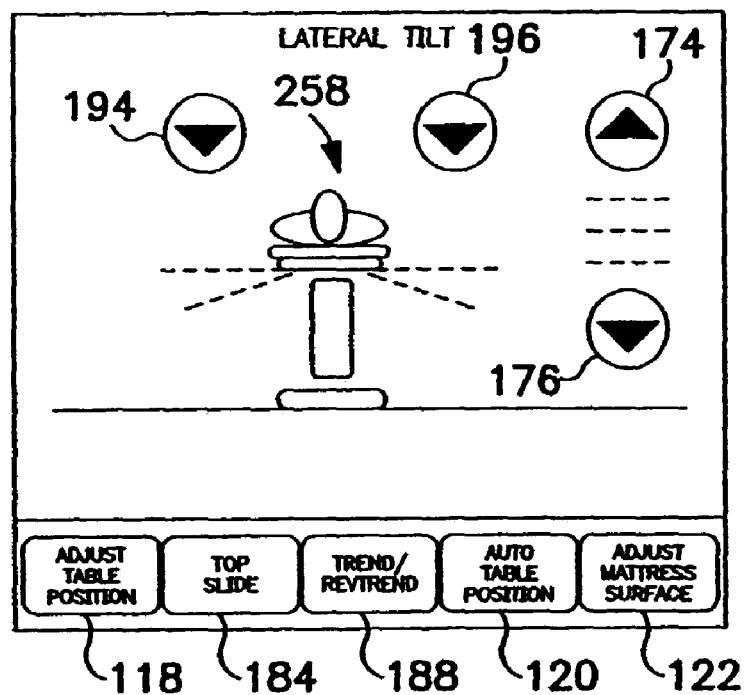
FIG. 15 is a front view of a lateral tilt screen similar to FIG. 12, showing input indicators for tilting the table about a longitudinal axis and for adjusting the vertical support column.

A lateral tilt display accessible via selection indicator 186 is provided for tilting table frame sections 84, 86, 88, 90, 92, 94 laterally relative to vertical support column 76 as shown in FIG. 15. Iconographic representation 258, which shows an end view of patient 54 atop table 42, is provided. Left and right tilt input indicators 190, 192 for tilting seat frame 58 and mattress 60 laterally relative to vertical support column 76 provide the "press and hold" capability as discussed above. Vertical up and down input indicators 174, 176 are also provided on display 116, as are table adjustment, top slide, Trendelenburg adjustment, automatic table adjustment, and mattress adjustment selection indicators 118, 184, 188, 120, 122.

Figure 16:
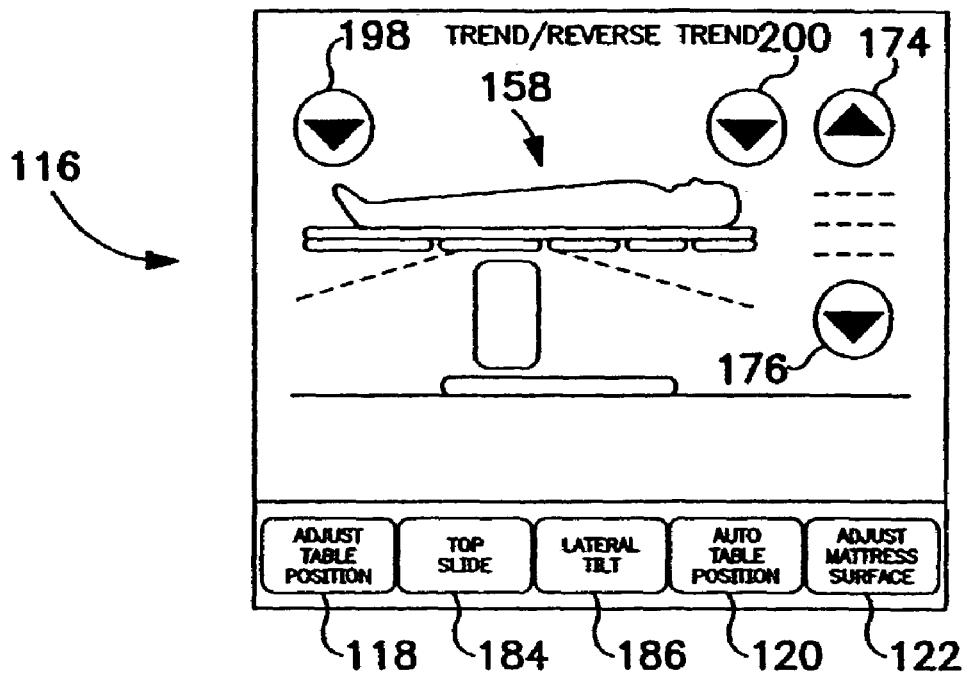
FIG. 16 is a front view of a Trendelenburg adjustment screen similar to FIG. 12, showing input indicators for tilting the table about a lateral axis and for adjusting the vertical support column.

A Trendelenburg display accessible via selection indicator 188 is provided for conjointly tilting table frame sections 84, 86, 88, 90, 92, 94 longitudinally relative to vertical support column 76 as shown in FIG. 16. Iconographic representation 158 is provided with frame 58 shown in a level configuration, although, as with the display of FIG. 14, a representation showing a current configuration of articulated sections 84, 86, 88, 90, 92, 94 can be provided. Foot end down and head end down input indicators 198, 200 for tilting frame 58 longitudinally relative to vertical support column 76 provide "press and hold" capability as discussed above. Vertical up and down input indicators 174, 176 are also provided on display 116, as are table adjustment, top slide, lateral tilt, automatic table adjustment, and mattress adjustment display selection indicators 118, 186, 188, 120, 122.

Figure 17:
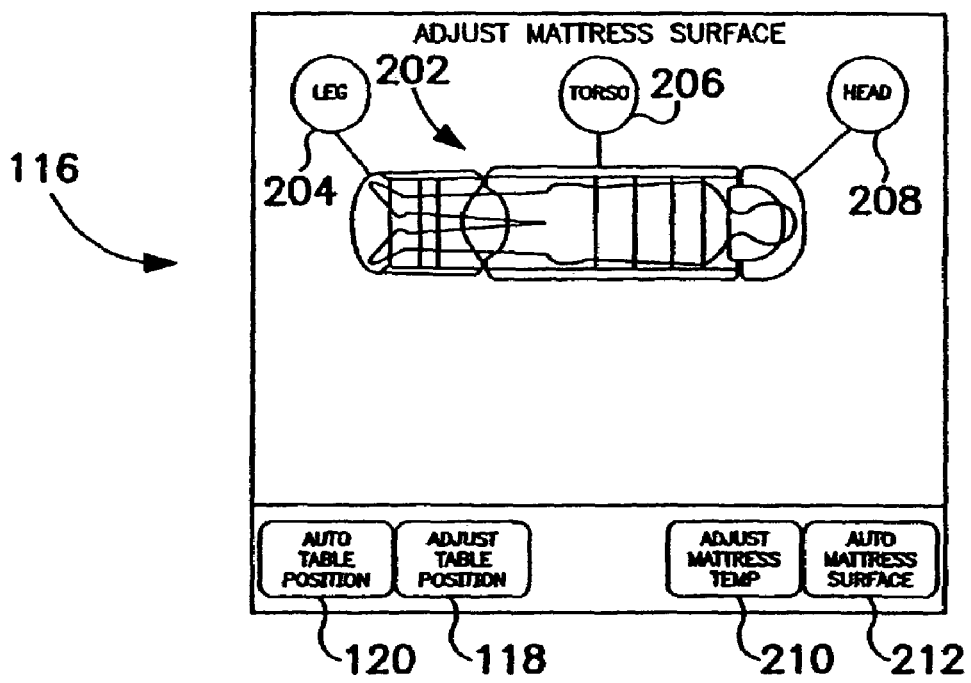
FIG. 17 is a front view of a mattress surface adjustment screen including an iconographic representation of a top view of a patient atop a mattress, with selection indicators for selecting leg, torso, and head adjustment functions, and including selection indicators along the bottom of the display to access mattress temperature adjustment and automatic mattress surface adjustment screens.

A mattress adjustment display accessible via selection indicator 122 is provided for controlling features of mattress 60 as shown in FIG. 17. A pictogram or iconographic representation 202 depicts a plan view of patient 54 atop mattress 60 showing various chambers with leg, torso, and head mattress sections. Selection indicators 204, 206, 208 are provided for selecting further screens for controlling leg 102, torso 100, and head 96, 98 sections of mattress 60. Automatic table adjustment, table adjustment, mattress temperature adjustment, and automatic mattress adjustment display selection indicators 118, 120, 210, 212 are provided near display 116 bottom.

Figure 18:
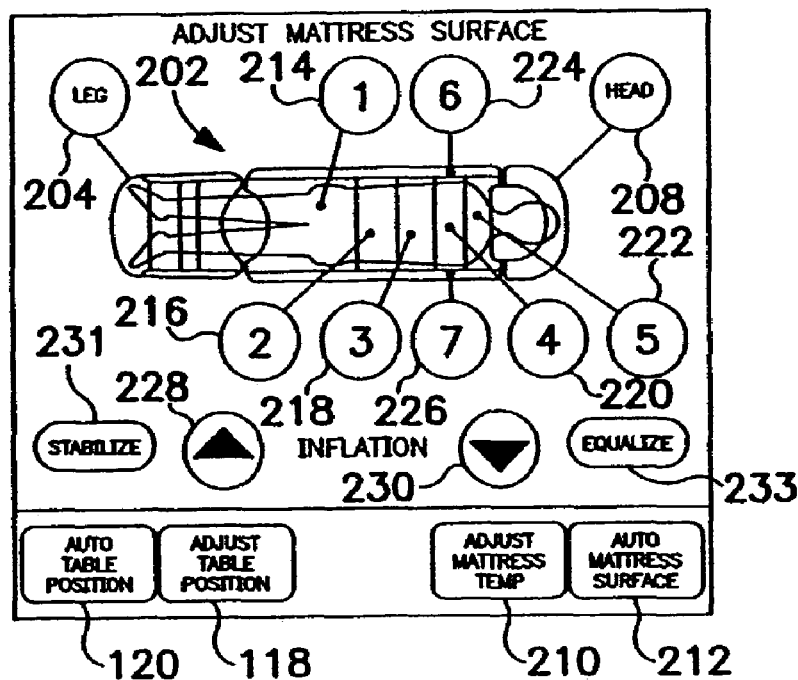
FIG. 18 is a front view of a mattress surface adjustment screen similar to FIG. 17 with a torso section of the mattress selected for adjustment, and including selection indicators for selecting regions of the torso section of the mattress for adjustment, input indicators for increasing or decreasing pressure in a selected region, and input indicators for stabilizing the mattress surface or to equalize mattress pressure.

A torso mattress adjustment display accessible via torso selection indicator 204 is provided for controlling torso section 100 of mattress 60 as shown in FIG. 18. Iconographic representation 202 and leg and head mattress section selection indicators 204, 208 are provided as shown in FIG. 17. Torso mattress section chamber selection indicators 214, 216, 218, 220, 222, 224, 226 are provided near their corresponding locations on iconographic representation 202, along with lines indicating the correspondence. One or more mattress section chambers can be selected by depressing its indicator, which results in a reverse video display of that indicator to indicate its selection. Inflation increase and decrease input indicators 228, 230 are provided for increasing or decreasing pressure in one or more selected mattress sections, using a "press and hold" paradigm as discussed above.

Stabilize input indicator 231 and equalize input indicator 233 are provided near increase and decrease input indicators 228, 230. The stabilize feature stiffens one or more selected sections of vacuum bead mattress 60 by creating a vacuum in the corresponding chamber(s) to withdraw fluid from selected section(s). The equalize feature adjusts selected mattress sections to a baseline level by setting pressure in corresponding chambers to a baseline level to prepare for a new patient or procedure. The torso mattress adjustment display also includes automatic table adjustment, table adjustment, mattress temperature adjustment, and automatic mattress adjustment selection indicators 120, 118, 210, 212 displayed along the bottom of display 116. Similar display screens (not shown) are provided for controlling leg and head sections 102, 96, 98 of mattress 60.

Figure 19:
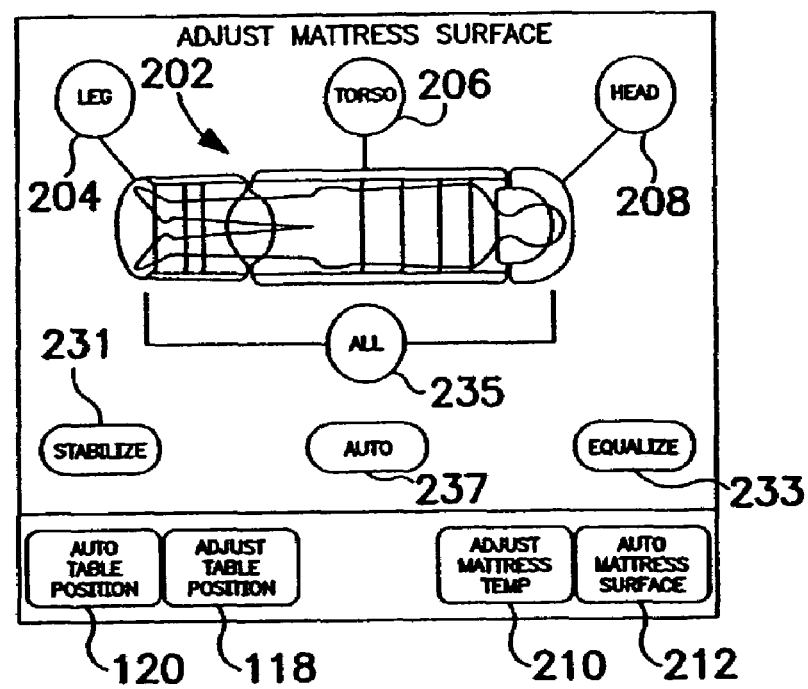
FIG. 19 is a front view of an automatic mattress surface adjustment screen similar to FIG. 17, including selection indicators for selecting some or all portions of the mattress for adjustment and input indicators for stabilizing, equalizing, or automatically adjusting the entire mattress by sensing pressure in each mattress region and controlling each region to conform the mattress to the patient's body.
Figure 20:
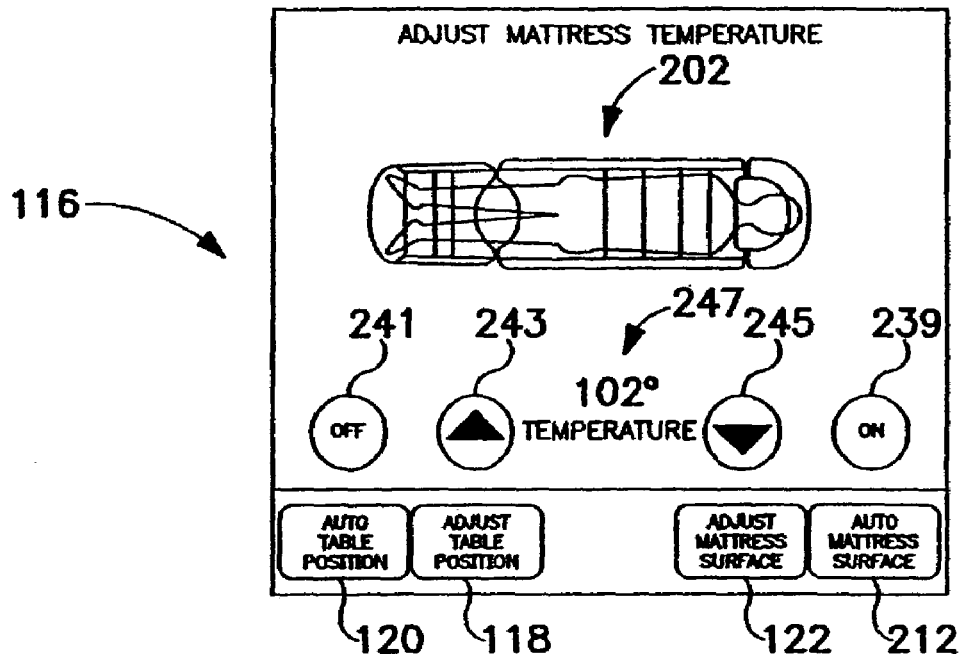
FIG. 20 is a front view of a mattress temperature adjustment screen similar to FIG. 17, including a temperature display and input indicators for enabling or disabling temperature control and for increasing or decreasing a designated temperature.

An automatic mattress adjustment display accessible via automatic mattress adjustment selection indicator 212 includes iconographic representation 202, leg, torso, and head mattress section selection indicators 204, 206, 208, an all mattress section selection indicator 235, and stabilize, equalize, and automatically adjust input indicators 231, 233, 237 as shown in FIG. 19. The all mattress selection indicator 235 provides a shorthand mechanism for selecting all sections. The stabilize and equalize functions work as discussed above for FIG. 18, except that all chambers within a selected mattress section are automatically designated for a selected mattress section. Selection of automatically adjust input indicator 237 uses pressure sensors within each chamber or cell (not shown) coupled to mattress 60 to conform mattress 60 automatically to a patient's body by varying pressures to each chamber based on sensed pressure. As with FIG. 18, automatic table adjustment, table adjustment, mattress temperature adjustment, and automatic mattress adjustment selection indicators 120, 118, 210, 212 displayed along the bottom of display 116.

A mattress temperature adjustment display accessible via mattress temperature adjustment selection indicator 210 includes iconographic representation 202, temperature subsystem on and off buttons 239, 241 for enabling or disabling the temperature control subsystem, target temperature increase and decrease input indicators 243, 245, and a target temperature display value 247. This display illustrates control of an optional temperature control subsystem (not shown) that controls the entire mattress temperature to a particular target value, such as by using a temperature controlled fluid supply to the mattress, a thermal-resistive covering of the mattress, etc. Those skilled in the art will understand that further temperature control features can be provided, such as separate temperature control for different mattresses regions or sections, display of actual temperature(s) of the mattress surface, facilities for cycling temperature over various periods and ranges, etc. This highlights a basic advantage of controller 40's architecture, which facilitates integration of additional features or controlled subsystems into a single interface.

Controller 40 further provides for programming and storing desired configurations of table frame 58 and mattress 60 for subsequent recall from auto adjust menu 132. A "save config" input indicator (not shown) provided from appropriate display screens such as the adjust table screens of FIGS. 13A and 13B provides access to a "save named configuration" screen (not shown) that prompts the user for entry of a configuration name through use of an alphabetic keypad provided on display 116. Management functions for manipulating saved configurations further provide for deleting, renaming, reordering, etc. of stored configurations.

Referring now to FIGS. 22–24, controller 40 is designed to support its use by either a left-handed or right-handed operator. An essentially "ambidextrous" device is provided by housing 114 and display 116 that are substantially symmetric about a longitudinal axis 261 of controller 40. Housing 114 has relatively flat front and back surfaces 249, 251 coupled by rounded side edges 253, bottom edge 263, and top edge 265. Display 116 and power button 115 are coupled to front surface 249. As best shown in FIGS. 23 and 24, display 116 covers most of front surface 249 of housing 114 so that a relatively large display with large, easy-to-see touch-screen buttons are provided in a portable, hand-held unit.

Housing 114 includes a handle 255 appended to back surface 251. Handle 255 is configured with a cylindrical shape having a somewhat elliptical cross-section to facilitate ease of grasping and holding. Handle 255 is configured to retain rechargeable batteries (not shown) that provide power for controller 40. The cylindrical shape of handle 255 further facilitates coupling controller 40 to a retaining socket (not shown) for temporary or permanent storage. The retaining socket can be provided on an IV pole, equipment bracket, or wall, or anywhere in an operating room environment, and is configured to provide for battery recharging either with a direct voltage coupling or through an indirect magnetic field charging system. Handle 255 further provides a support to allow for sitting controller 40 upright by placing controller bottom surface 263 on a table or other surface. Although a generally cylindrical handle 255 is shown, those skilled in the art will see the abundance of variations possible for configuring alternative handles to facilitate holding controller 40 and coupling it to items found throughout the operational environment, such as an operating room, to facilitate temporary or permanent storage of controller 40.

Figure 27:
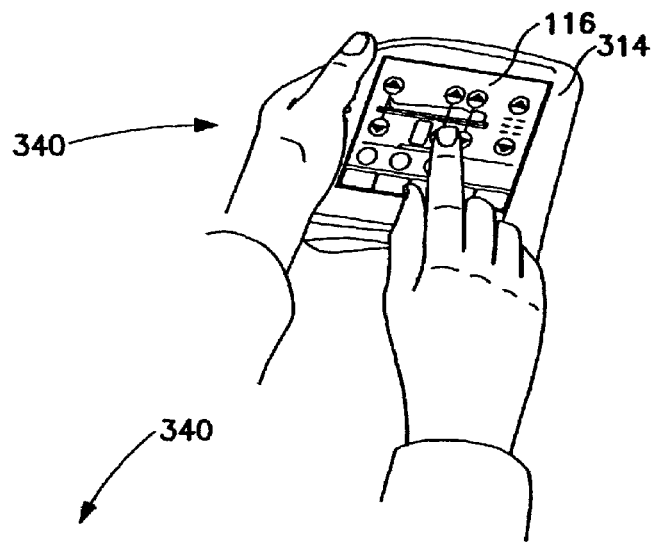
FIG. 27 is a perspective view of the controller of FIG. 22 showing a right-handed user interface.
Figure 25:
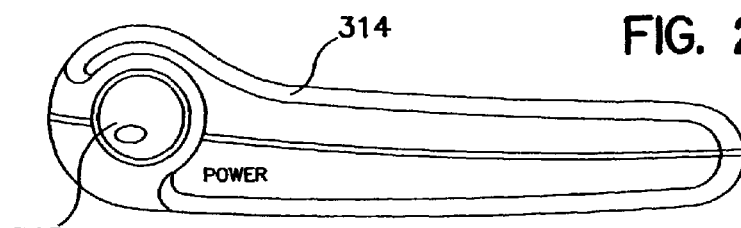
FIG. 25 is a top plan view of another embodiment of a medical device controller similar to the embodiment of FIGS. 9–11, showing a housing profile with a power button and configured for holding by a left hand.
Figure 26:
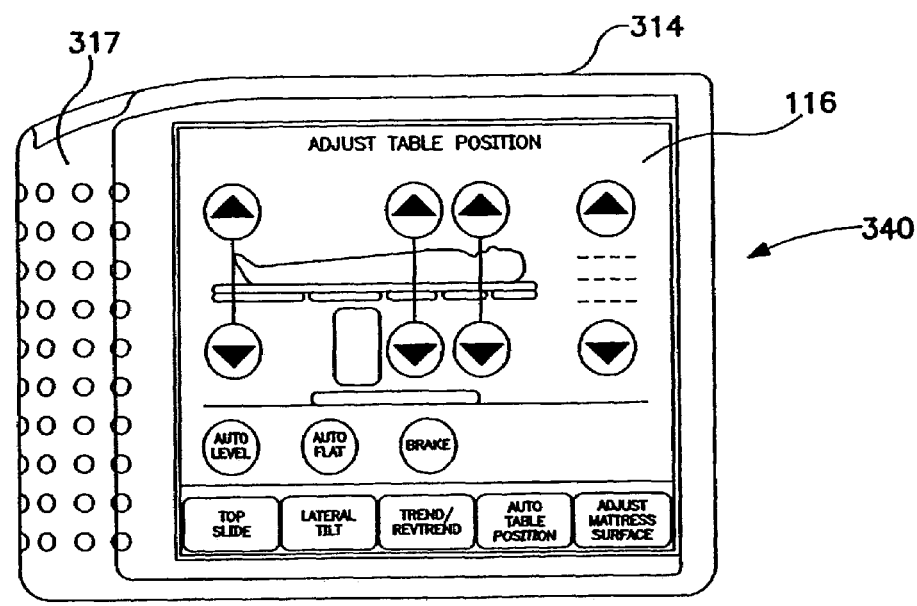
FIG. 26 is a front elevation view of the controller of FIG. 22, showing a gripping surface and a display.

Referring now to FIGS. 25–27, an alternative embodiment controller 340 is provided that includes the same display 116 as controller 40, mounted in an asymmetric housing 314 and having a side-mounted power button 315. Controller 340 includes a left-handed gripping surface 317 so that operation of touch-screen buttons is made by a care giver's right hand. Controller 340 can, however, be programmed so that all screens are displayed "upside down", thus converting controller 340 from a right-handed configuration to a left-handed configuration. This shows the utility of the programmable architecture of the present invention.

Another alternative embodiment controller 440 is shown in FIGS. 28–33. Controller 440 includes a tapered housing 414 coupled to recessed power button 415, up and down buttons 402, 404, semi-circular adjust and select buttons 406, 408, a display 416, and a control cable 419. Like controller 40, housing 414 and display 416 are substantially symmetric about a longitudinal axis to permit equally simple use by left-handed or right-handed operators. Rather than using a touch-screen display, controller 440 uses only the four input buttons 402, 404, 406, 408, and varies the functions performed by these buttons based on the information presented and selected on display 416.

Controller 440 indicates a single selection of an item on display 416, such as a single controllable feature, a predefined overall configuration of a controlled system, or another controller option. Controller 440 provides for slewing designation of the selected item to other selectable items based on user input to select button 408. Pressing adjust button 406 when a predefined overall configuration is designated, such as one of the table configurations illustrated in FIGS. 30–33, results in controller 440 commanding the controlled system to assume the predefined configuration. As with controller 40, adjust button 406 can provide a "press and hold" capability. Pressing adjust button 406 when a controllable feature is designated allows for use of up and down buttons 402, 404 to control the designated feature, such as moving a particular section of an articulated surface, or controlling pressure of a portion of a controllable mattress, etc. Pressing adjust button 406 when another controller option is designated will result in controller 440's displaying of another display screen with selectable items.

Yet another alternative embodiment controller 540 is shown in FIGS. 34–38. Controller 540 includes a tapered housing 514 coupled to recessed power button 415, up and down buttons 402, 404, pie-shaped adjust, select, and equipment buttons 506, 508, 510, a display 516, and a control cable 519. Like controllers 40 and 440, housing 514 and display 516 are substantially symmetric about a longitudinal axis to permit equally simple use by left-handed or right-handed operators. Controller 540's display 516 is the same as display 416, with controller 540 similarly programmed to provide information on display 516, such as an iconographic representation 558, along with other indicia indicating controllable features and other selectable controller menu options. Iconographic representation 558 varies to represent the controlled system by displaying a stylized lighthead as shown in FIG. 36, temperature display as shown in FIG. 37, and surgical table as shown in FIG. 37. A light intensity indicator bar 560 is provided as shown in FIG. 36, which varies an amount displayed in reverse video to represent the percentage light intensity currently being output by the lighthead. Similarly, the temperature display of FIG. 37 is updated to indicate an actual controlled temperature value, and the iconographic table representation of FIG. 38 is presented in correspondence with the current surgical table configuration.

Operation of controller 540 is the same as for controller 440 except that controller 540 includes equipment button 510, which is used to switch between different controlled systems. Thus, rather than selecting a displayed item to switch between controlled systems, controller 540 automatically toggles between controlled systems when an operator presses equipment button 510. This provides a convenient mechanism for quickly switching via single press of a button to a desired system, such as the lighting system of FIG. 36, the temperature control system of FIG. 37, and the table system of FIG. 38.

Yet another alternative embodiment controller 640 includes a handheld housing 614, a display 616, eight pairs of buttons 650 . . . 680, and a power button 682 as shown in FIGS. 39–40. Controller 640, including its buttons 650 . . . 682, is symmetric about a longitudinal axis 661 to facilitate ambidextrous use. Buttons 650 . . . 680 include indicia that represent their respective table control functions and provide "press and hold" control as discussed above. Buttons 650, 652 provide a table high/low functions, buttons 654, 656 provide Reverse/Reverse Trendelenburg functions, buttons 658, 660 provide lateral tilt left/right functions, buttons 662, 664 provide back up/down functions, buttons 666, 668 provide upper back up/down functions, buttons 670, 672 provide leg up/down functions, buttons 674, 676 provide slide lower/upper functions, button 678 provides an auto flat function, and button 680 provides a high speed button to increase table speed when depressed simultaneously with another of buttons 650 . . . 678. Controller 640 provides a sealed housing that is durable, easy to clean, and suitable for use in sterile environments. Buttons 650 . . . 680 are backlit to enhance ease of use, and display 616 provides graphic functionality similar to controllers 40, 340, 440, 540 discussed above. Controller 640 can be a pendant controller tethered to table 42 similar to controller 81 of FIG. 2 or can be configured as a wireless controller.

As detailed above, the controllers 40, 340, 440, 540, and 640 each may be wired directly to controllable devices, or may be configured to send signals to the controllable devices using a wireless link, such as a radio frequency (RF), infrared (IR), or ultrasound communication link. By using a wireless link, the controller 40, 340, 440, 540, and 640 may be conveniently moved around the operating room environment by a care giver 56. While each controller 40, 340, 440, 540, and 640 is mobile to increase room efficiency, the mobility of the controller 40, 340, 440, 540, and 640 also allows the controller 40, 340, 440, 540, and 640 to be removed from the operating room. Removal of the controller 40, 340, 440, 540, and 640 is usually not desirable in that the gained efficiency is lost when the controller 40, 340, 440, 540, and 640 can not be located by the caregiver 56.

As such, in a further illustrative embodiment of the invention, a proximity alarm system 710 including a locating or proximity sensing device is associated with the controller 740. The controller 740 illustratively includes an alarm 754 that alerts a user or caregiver 56 attempting to transport the controller 740 away from a predetermined location or item, such as the controllable medical device, or the room within which the controllable medical device is located. The alarm 754 may comprise an audible alarm, such as a horn or buzzer. Alternatively, the alarm may comprise a visual alarm, such as a light, or a vibratory alarm for providing a tactile sensation to a person in proximity to the alarm. Further, the alarm 754 may be in the form of an electronic transmission to a personal computer, portable data assistant, cellular phone, pager, or other similar portable device.

In the following description, the controllable medical device will be described as a patient support, such as surgical table 42. However, it should be appreciated that the controller 740 may be coupled to other controllable medical devices, such as surgical lighting system 44, as detailed above. Other aspects of the controller 740 may be substantially the same as those detailed above with respect to controller 40.

Figure 41:
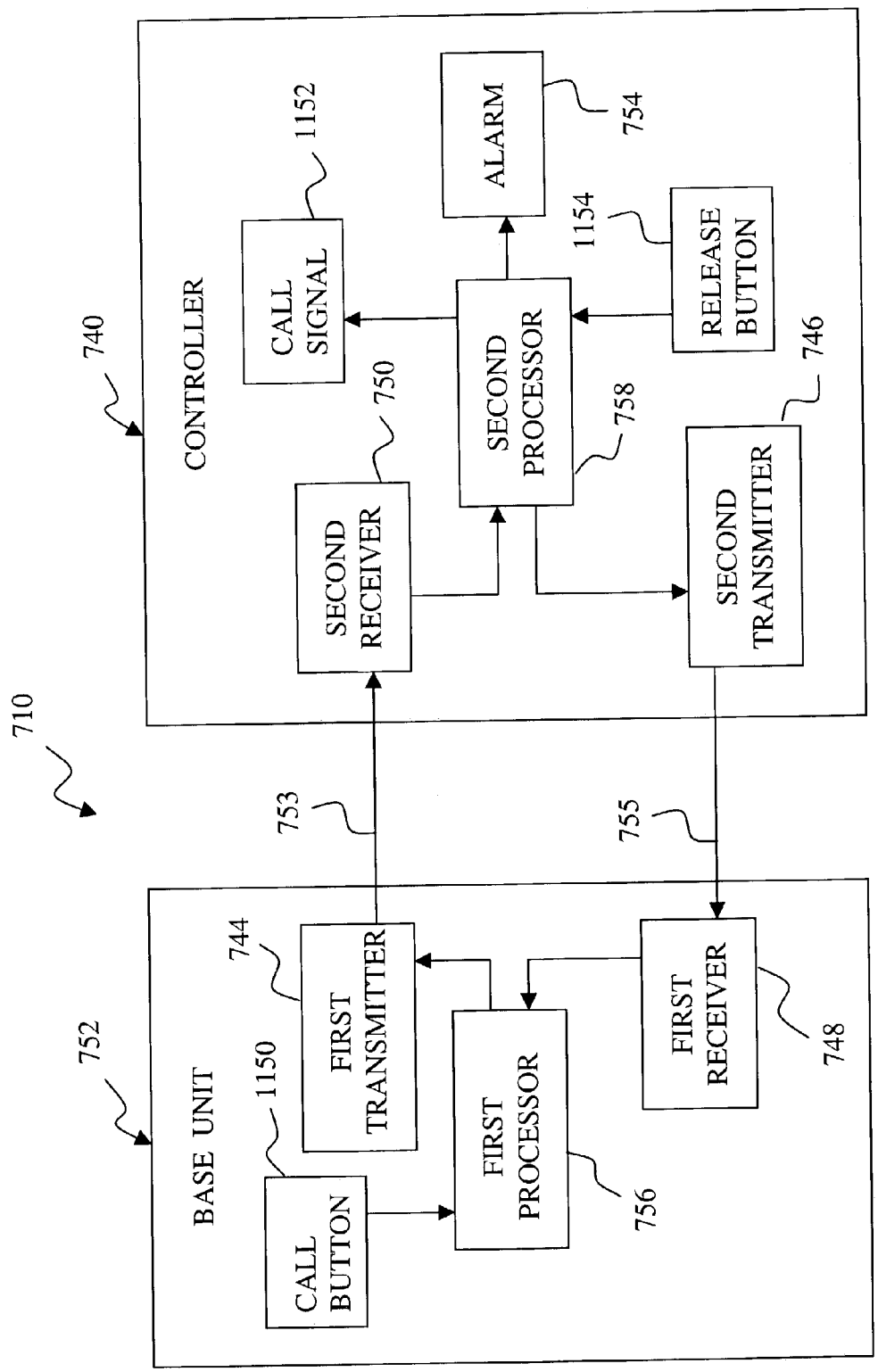
FIG. 41 is a block diagram showing communication between a base unit and a controller of an illustrative embodiment proximity alarm system of the present invention.

There are several different embodiments of proximity alarm system 710 which may be associated with the controller 740. In a first illustrative embodiment as shown in FIG. 41, proximity alarm system 710 includes transmitters 744, 746 and receivers 748, 750 of signals carried by a wireless energy source, such as radio frequency (RF), infrared (IR), or ultrasound. A first transmitter 744 and a first receiver 748 are associated with the controllable medical device, and are illustratively located in a base unit 752 coupled to the patient support 42. A second transmitter 746 and a second receiver 750 are coupled to the housing 114 of the controller 740. The first transmitter 744 of the base unit 752 illustratively emits a radio frequency (RF) signal 753 that is received by the second receiver 750 of the controller 740. In response, the second transmitter 746 of the controller 740 sends out a RF signal 755 that is received by the first receiver 748. By measuring the time difference between the signal transmission by the first transmitter 744 and the signal receipt by the first receiver 748, knowing the speed of the RF signals 753 and 755, and knowing the processing signal turn around time at the controller 740, the distance between the controller 740 and the base unit 752 can be determined. If the distance is larger than a predetermined maximum, the alarm 754 is activated. The alarm 754 is preferably located at the controller 740, but may be at the base unit 752 or elsewhere. The predetermined maximum distance may be customized as desired.

In the illustrative embodiment of FIG. 41, assuming that time-alignment of the base unit 752 and the controller 740 is achieved, the second receiver 750 of controller 740 is initially in a receive-only mode waiting for the RF signal 753 from first transmitter 744 of the base unit 752 which has been suitably coded by a modulation coder, illustratively incorporated within a first processor 756. When the second receiver 750 of the controller 740 receives the transmitted signal 753, a second processor 758 demodulates the signal 753, and logically checks the frequency and/or code. The second processor 758 illustratively includes a phase-locked loop oscillator (not shown) which is locked in a frequency and phase relationship with a control oscillator (not shown) of the first processor 756 of the base unit 752. The second processor 758 then switches off the second receiver 750 and causes the second transmitter 746 to transmit RF signal 755 back to the base unit 752, suitably coded, and on a different frequency after amplifying the signal 755 through an amplifier (not shown).

Meanwhile, the first processor 756 of the base unit 752 has turned off the first transmitter 744 and has caused the first receiver 748 to enter a receive mode. When the first receiver 748 of the base unit 752 receives the transmitted signal 755 from the controller 740, the processor 756 demodulates the signal 755, checks the code, and applies the modulating component to a phase detector of the first processor 756 to compare the phase of the returning signal 755 against its reference oscillator. The phase-shift of the demodulated signal 755 corresponds to the round-trip time-delay between the base unit 752 and the controller 748 and can be used to operate a suitably calibrated meter to indicate the distance or range between the base unit 752 and the controller 740. Additional details of the alarm system 710 may be of the type disclosed in U.S. Pat. No. 4,908,627, the disclosure of which is expressly incorporated herein by reference.

Figure 42:
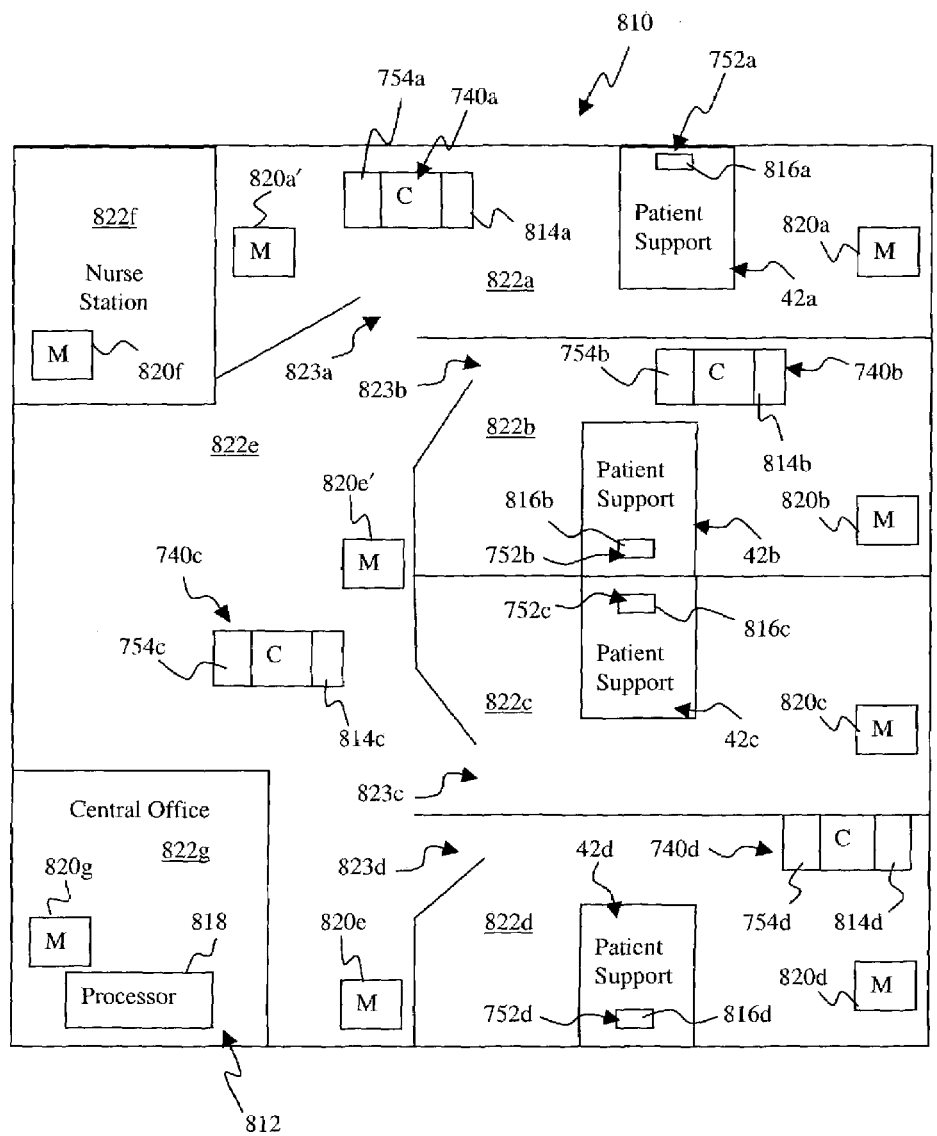
FIG. 42 is a diagrammatical representation of a portion of a healthcare facility incorporating another illustrative embodiment proximity alarm system.

In a further illustrative embodiment as shown in FIG. 42, a proximity alarm system 810 operates by being integrated with a tracking system 812. In one illustrative embodiment, the tracking system 812 separately tracks two items, such as the controller 740 and the base unit 752. More particularly, the controller 740 and the base unit 752 have identification (ID) tags 814 and 816, respectively, coupled to them and which are identifiable and trackable by the tracking system 812. The tracking system 812 is configured to link ID tags 814 and 816 in a central tracking computer or processor 818. ID tags 814 and 816 that are linked are known by the processor 818 to be associated and required to remain within a predetermined proximity to each other. The alarm system 810 communicates with the tracking system 812, which tracks both linked items 740 and 752, and either determines the distance between them or determines if they are located in the same room 822. A determination that the distance between the linked items 740 and 752 exceeds a predetermined value, or that the linked items 740 and 752 are in different rooms 822, causes the processor 818 to activate the alarm 754.

The tracking system 812 includes a plurality of monitors or detectors 820 positioned in different locations within a care facility, a hospital, or other area being monitored. The monitors 820 may comprise conventional receivers or transceivers, and each room 822 of the hospital typically includes at least one monitor 820. The monitors 820 each include a sensor to detect identification (ID) signals being generated by the tags 814 and 816 and/or to excite the tags 814 and 816 to generate the ID signals. If monitors 820 in different rooms 822 each sense one of linked tags 814 and 816, then the processor 818 knows that linked items 740 and 752 have been separated and the alarm 754 is activated. In the following description, each component associated with a particular room 822 is identified by its reference number followed by a letter corresponding to a particular room 822a, 822b, 822c, 822d, and 822e, respectively.

With further reference to FIG. 42, illustratively the monitor 820c associated with room 822c detects tag 816c coupled to base unit 752c. However, the monitor 820e' associated with hallway 822e detects tag 814c coupled to controller 740c. Signals sent from the monitors 820c and 820e' are received by the processor 818 which determines that the controller 740c is located in hallway 822e while the base unit 752c is located in room 822c. In response, the processor 818 activates the alarm 754c located within the controller 740c to provide an alert to the caregiver 56 that the controller 740c has been separated from the patient support 42c by an unacceptable distance.

Alternatively, the processor 818 knows the position of each monitor 820 and the distances between the monitors 820. The monitors 820 then locate the linked ID tags 814 and 816 by triangulation or other conventional method, and compare the locations of linked tags 814 and 816. When the distance between the linked items 740 and 752 exceeds the predetermined value, the alarm 754 is activated. For example, with further reference to FIG. 42, room 822a includes first and second monitors 820a and 820g which together provide information regarding locations of the tags 814a and 816a to the processor 818. If the processor 818 determines that the linked items 740a and 752a have become separated by an amount exceeding a predetermined value, then the processor 818 activates the alarm 754a located within the controller 740a.

In one illustrative embodiment, the locations of the controller 740 and the base unit 752 are each determined by identifying which monitor 820 receives an ID signal from respective tags 814 and 816 associated therewith. An infrared (IR) line-of-sight tracking system is one type of such locating and tracking system. Another illustrative type is passive RF transmitters and absolute reference position (ARP) sensors. The system knows that the controller 740 and the base unit 752 are generally in the area of the monitor(s) 820 receiving the signals from the tags 814 and 816. In one variation, signal strength of the ID signals received from the tags 814 and 816 are used to better approximate the location of the corresponding controller 740 and base unit 752 relative to the monitor(s) 820. In another variation, the tags 814 and 816 are interrogated or caused to send the respective ID signals and the respective times it takes for the signals to reach the monitor(s) 820 are used to better approximate the location of the corresponding controller 740 and base unit 752 relative to the monitor(s) 820.

In another example, the locations of the controller 740 and the base unit 752 are each determined by two or more fixed-location monitors 820 that each receive an ID signal from the respective tag 814 and 816 associated therewith. Such systems determine the location of the controller 740 and the base unit 752 by determining a distance measurement for each monitor 820 that is indicative of the distance from the respective monitor 820 to the respective tag 814, 816. The distance measurements for the monitors 820 are then used to determine the location of the controller 740 and the base unit 752 in either two dimensions or three dimensions. In one variation, the distance measurements are based on the time it takes for the ID signal from the tag 814, 816 to reach each monitor 820. In another variation, the distance measurements are based on the signal strength of the ID signal received at each monitor 820. In yet another variation, the distance measurements are based on a combination of both time and signal strength. The location of the controller 740 and the base unit 752 may be classified as being within a given region or zone of an area of interest or as being within a sphere of space having a center that corresponds to the best approximation of the location of the respective controller 740 and base unit 752 and a periphery corresponding to the resolution of the system.

Additional details regarding location determination from tracking system 812 are disclosed in U.S. Provisional Patent Application Ser. No. 60/462,216, filed Apr. 11, 2003, which is assigned to the assignee of the present invention and the disclosure of which is expressly incorporated by reference herein.

Figure 43:
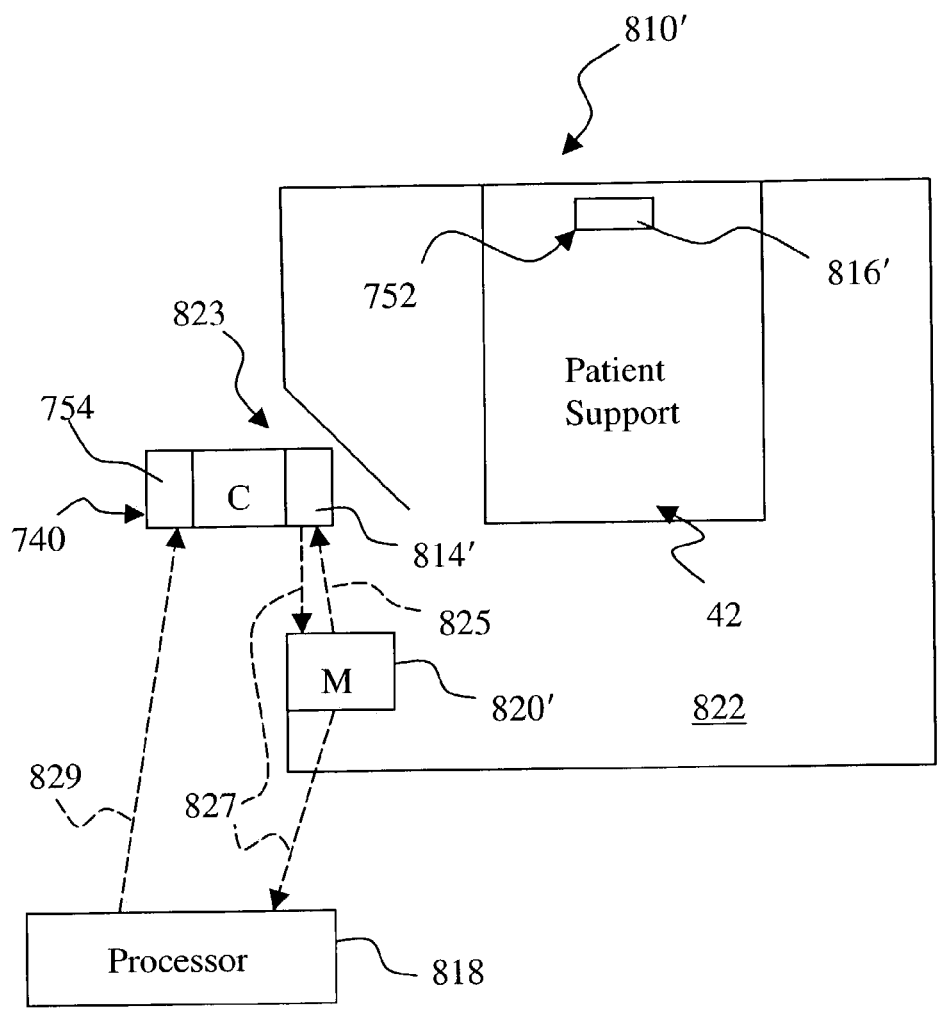
FIG. 43 is a diagrammatical representation of a room of a healthcare facility incorporating a further illustrative embodiment proximity alarm system.

In another embodiment proximity alarm system 810' utilizing ID tags 814' and 816', the monitors 820 are configured to monitor the entrances/exits, illustratively the doorways 823 of rooms 822 as shown in FIG. 43. The processor 818 is configured to activate the alarm 754 when one of the ID tags 814' and 816' passes through, or within proximity of, the doorway 823. In such an embodiment, items 740 and 752 that belong in a certain area or room 822 can be retained in that room 822. The processor 818 in such an embodiment may be instructed to allow passage of first and second ID tags 814' and 816' into and out of the room 822 when the linked first ID tag 814' enters or leaves the room 822 with the second linked ID tag 816'. Furthermore, in cases where an item needs to be serviced, the processor 818 may be instructed to allow passage of the item 740, 752 and the associated ID tag 814', 816' through the monitored doorway 823.

As illustrated in FIG. 43, each ID tag 814' and 816' comprises a transponder tag which is physically connected to the controller 740 and the base unit 752, respectively. The monitor 820' illustratively comprises an exciter/reader located at a respective doorway 823 such that the tagged items 740 and 752 must pass by the monitor 820' before exiting the room 822. The monitor 820' generates and transmits a surveillance excitation signal 825, which is illustratively an RF signal, but may comprise any wireless signal including IR or ultrasound. When within a receiving range of the monitor 820', the tags 814', 816' receive the RF surveillance excitation signal 825 and, in the absence of a deactivation instruction, respond thereto by generating and transmitting a surveillance response signal 827, which again is illustratively an RF signal but may comprise any wireless signal. The monitor 820' receives the RF surveillance response signal 827 which is then transmitted to the processor 818 which, in turn, activates the respective alarm 754 through an alarm signal 829. Additional details of the alarm system 810' may be similar to those detailed in U.S. Pat. No. 5,874,896, the disclosure of which is expressly incorporated herein by reference.

In an additional illustrative embodiment, a plurality of monitors 820' may act as exciters/readers and generate excitation signals 825 which are received by tags 814' and 816'. Both tags 814' and 816' receive the generated excitation signals from the monitors 820' and generate ID signals, or surveillance response signals 827, corresponding to the respective tag 814' and 816'. In one example, the excitation signals 825 include a monitor ID, and the surveillance response signals 827 include a tag ID and the received monitor ID. By including the tag ID along with the received monitor ID, monitors 820' are able to determine which tags 814' and 816' are responding. A distance measurement between tags 814' and 816' may be determined by monitors 820' by comparing the round trip time (from generation of the excitation signal 825 to reception of the respective surveillance response signal 827) to receive surveillance response signals 827 by each of the monitors 820'.

In another illustrative embodiment, a single monitor 820' may be provided in an area or room 822 along with multiple fixed exciters (not shown). Each exciter is configured to generate an excitation signal 825, which is received by monitor 820' and by tags 814' and 816'. Each excitation signal 825 includes a unique ID to identify the respective exciter. Tags 814' and 816', in response to receiving an excitation signal 825, generates an ID signal, or surveillance response signal 827, which includes a unique ID associated with respective tags 814' and 816' and the unique ID of the exciter(s), which generated the received excitation signal.

Additional details regarding the use of excitation signals 825 in locating and tracking systems are provided in U.S. Provisional Patent Application Ser. No. 60/462,216, the disclosure of which is expressly incorporated by reference herein.

The tags 814 and 816 of FIG. 42 may each include data about the base unit 752 of the patient support 42 and the controller 740, such as a unique item identifier. Tags 814 and 816 and the associated data gathering system described below may employ a variety of different technologies and incorporate the locating and tracking system 812. For example, tags 814 and 816 may include a transmitter similar to that detailed above in base unit 752 and controller 740 of proximity alarm system 810, and a memory, or use bar-code technology to store and convey the data. Again, tags 814 and 816 may operate utilizing any conventional wireless technology, including RF, IR, and ultrasound.

In an illustrative embodiment, tags 814 and 816 may include a radio frequency identification (RFID) device (either active or passive) for providing the data to a receiver as described below. Such RFID devices are produced, for example, by Intermec Technologies Corporation of Everett, Wash. RFID tags 814 and 816 may be configured for read-only operation, volatile read/write operation, or write once/read many (WORM) operation. Such tags 814 and 816 do not require contact or line-of-sight reading.

Figure 44:
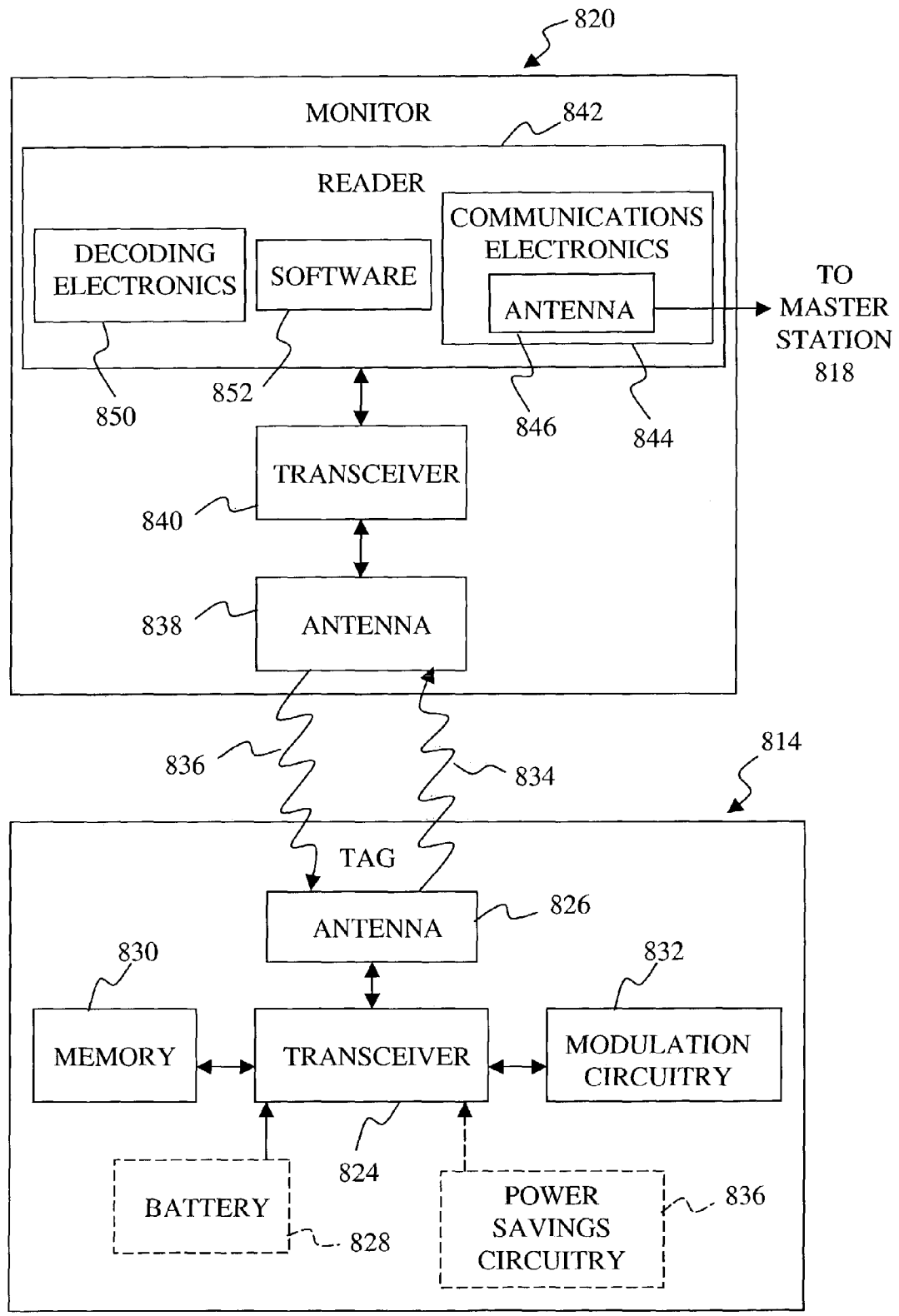
FIG. 44 is a block diagram showing communication between a monitor and an RFID tag of the proximity alarm system of FIG. 42.

As shown in FIG. 44, active RFID tags 814 and 816 are substantially identical and may each include a transmitter, and a receiver (or a transceiver 824), an antenna 826, and a battery 828 to provide power to transceiver 824. Tag 814, 816 may further include a memory 830 to store data relating to its respective item 752 and 740, and modulation circuitry 832 to provide a tag signal 834 conveying such information as further described below. In an alternate embodiment, active RFID tags 814, 816 may further include a conventional power savings circuit 836 that interrupts or reduces the supply of power to the tag components when tag 814, 816 remains inactive (does not transmit or receive information) for a predetermined period of time. Tag 814, 816 remains in this power savings mode until it next receives a signal from a monitor or detector 820 as further described below.

Passive RFID tags 814, 816 may include similar components. Typically, passive RFID tags 814, 816 reflect RF signals received from detectors 820, and add information relating to item 740, 752. More specifically, when tag 814, 816 comes with range of a detector 820, the tag's antenna 826 receives an RF detector signal 836 transmitted by detector 820. Signal 836 may also be used to provide power to tag 814, 816 as is well-known in the art. Thus, passive RFID tags 814, 816 may not include a battery 828. Battery 828 may, however, be included in passive RFID tags 814, 816 to provide power to tag memory 830 (if any), or modulation circuitry 832. After detector signal 836 is received, tag modulation circuitry 832 encodes a tag signal 834 with the desired information (such as the unique item identifier). Tag signal 834 is then transmitted back to detector 820 either via the same antenna 826 that received detector signal 836, or another transmission antenna included on tag 814, 816.

Tags 814, 816 may be packaged in a variety of ways. For example, tags 814, 816 (including the transceiver, antenna, and any other components) may be enclosed within a container, case, or package adapted for attachment to item 740, 752 using adhesive, clips, or any other suitable attachment method. Alternatively, tags 814, 816 may be incorporated into a label for application (via adhesive or some other suitable attachment method) to item 740, 752. Such labels may be printed using special printers, such as those produced by Zebra Technologies of Vernon Hills, Ill., that employ printing technology similar to that employed by conventional bar-code printers.

Detector 820 for use with RFID tags 814, 816 generally includes an antenna 838, a transceiver 840, a reader 842, and communication electronics 844 including antenna 846 for wirelessly communicating with a central processing system, such as master processor or station 818. Of course, communication electronics 844 could alternatively be hardwired to master processor 818. Transceivers 840 transmit the RF energy of detector signal 836 to activate passive tags 814, 816 (or active tags 814, 816 in power savings mode) and power the response transmission (tag signal 834) from passive tags 814, 816. Generally, transceiver 840 is coupled to antenna 838 and reader 842. Antenna 838 generates an electrical field defining the range of detector 820. The antenna 838 may be incorporated into a doorway of patient rooms 822, a pass-through wall of a facility, a waste receptacle, a cabinet, or a variety of other structural elements or pieces of equipment.

Detector reader 842 controls the transmission of detector signals 836 by transceiver 840 and antenna 838, and receives and processes tag signals 834 from tags 814, 816 as received by antenna 838 and transceiver 840. Reader 842 includes communication electronics 844, decoding electronics 850 for decoding the information included in tag signals 834, and software 852. The decoded information is provided to communication electronics 844 for transmission to, for example, master processor 818. Software 852 may implement anti-collision algorithms as are commonly known in the art to permit substantially simultaneous reception of multiple tag signals 834.

By incorporating monitors 820 at various locations throughout the healthcare facility (e.g., doorways to patient rooms 822, operating rooms, recovery rooms, entryways to particular areas of the facility, etc.), the location of items 740, 752 equipped with tags 814, 816 may be automatically tracked using locating and tracking system 812.

Figure 45:
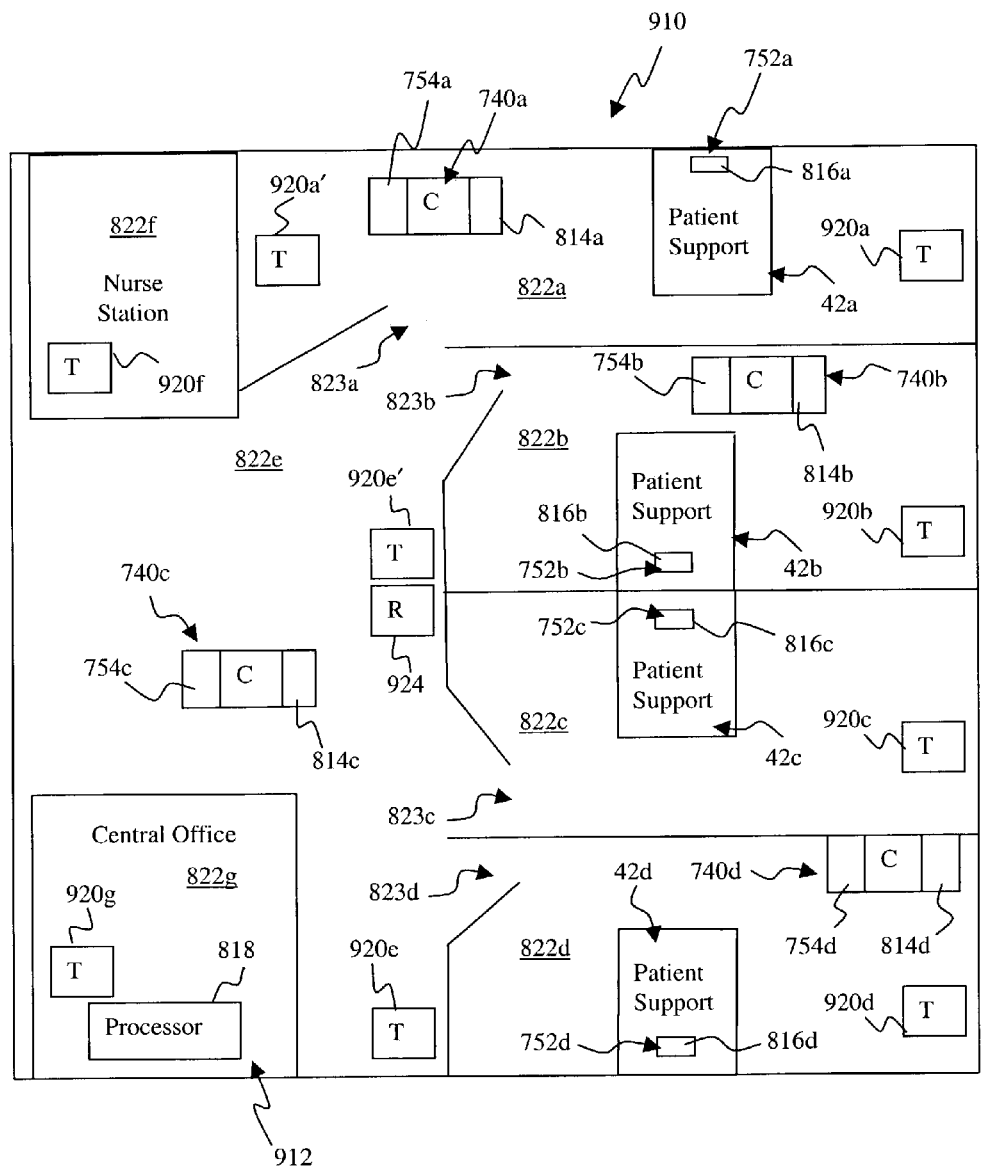
FIG. 45 is a diagrammatical representation similar to FIG. 42 illustrating another illustrative embodiment proximity alarm system.

Another illustrative tracking system 912 for use with the proximity alarm system 910 of the present invention is shown in FIG. 45. Those items in FIG. 45 with the same reference numbers as items in FIG. 42 identify like components.

The tracking system 912 includes a plurality of transmitters 920, at least one tag 814 associated with each controller 740, a receiver 924, and a central processor 818. Transmitters 920 are configured to generate an ID signal (not shown) containing a unique ID associated with the respective transmitter 920. The transmitter ID may be set by the setting of a conventional dip switch associated with each of transmitters 920. In one example, transmitters 920 include one of an IR transmitter, an ultrasound transmitter, or other line-of-sight transmitter. In another example, transmitters 920 include a low-frequency RF transmitter. Transmitters 920, in one example, include a battery (not shown) to provide power to generate the respective ID signal. In another example, transmitters 920 are coupled to a power supply (not shown) such as a facility electrical system.

Each tag 814 is configured to receive the ID signal generated by transmitters 920 when tag 814 is proximate to one of transmitters 920. Referring to FIG. 45, tag 814*b* receives the ID signal generated by transmitter 920*b* because tag 814*b* is located in patient room 822*b*. Each tag 814 is configured to generate an ID signal associated with the respective tag 814. The tag ID signal includes an ID unique to the respective tag 814 (controller 740) and at least the last received transmitter ID from one of transmitters 920. In one example, tag 814 generates an ID signal every time tag 814 receives a new transmitter ID, such as when tag 814 leaves the room 822 associated with the patient support 42 and enters hallway 822*e* proximate to transmitter 920*e*, 920*e*'. In another example, tag 814 generates a tag ID signal at a predetermined interval and includes all transmitter IDs received since the previously transmitted tag ID signal. In yet another example, tag 814 transmits the tag ID signal at two or more predetermined time intervals based on a characteristic of a displacement sensor (not shown) associated with tag 814. In the above examples, tag 814 is configured to store one or more transmitter IDs for later transmission in a tag ID signal.

Tag 814 includes an RF transmitter or other transmitter that is capable of sending the tag ID signal to receiver 924 which may be centrally located in facility. As such, the transmitters 920 associated with tags 814 must be capable of penetrating facility walls and other obstructions. Receiver 924 is connected to central computing device 818 through either a wired or wireless connection.

The location of transmitters 920 are stored in or otherwise made available to central computing device 818. As such, the location of tags 814 are determined by correlating the transmitter ID(s) transmitted with the tag ID signal with the known locations of transmitters 920. Central computing device 818 stores the location information related to each tag 814 for later processing or retrieval.

Additional details of illustrative locating and tracking systems 812 may be found in U.S. Pat. No. 6,462,656, U.S. patent application Ser. No. 10/154,644, filed May 24, 2002, U.S. patent application Ser. No. 10/265,781, filed Oct. 7, 2002, and U.S. Provisional Patent Application Ser. No. 60/462,216, filed Apr. 11, 2003, all of which have been assigned to the assignee of the present invention and the disclosures of which are expressly incorporated herein by reference.

Figure 46:
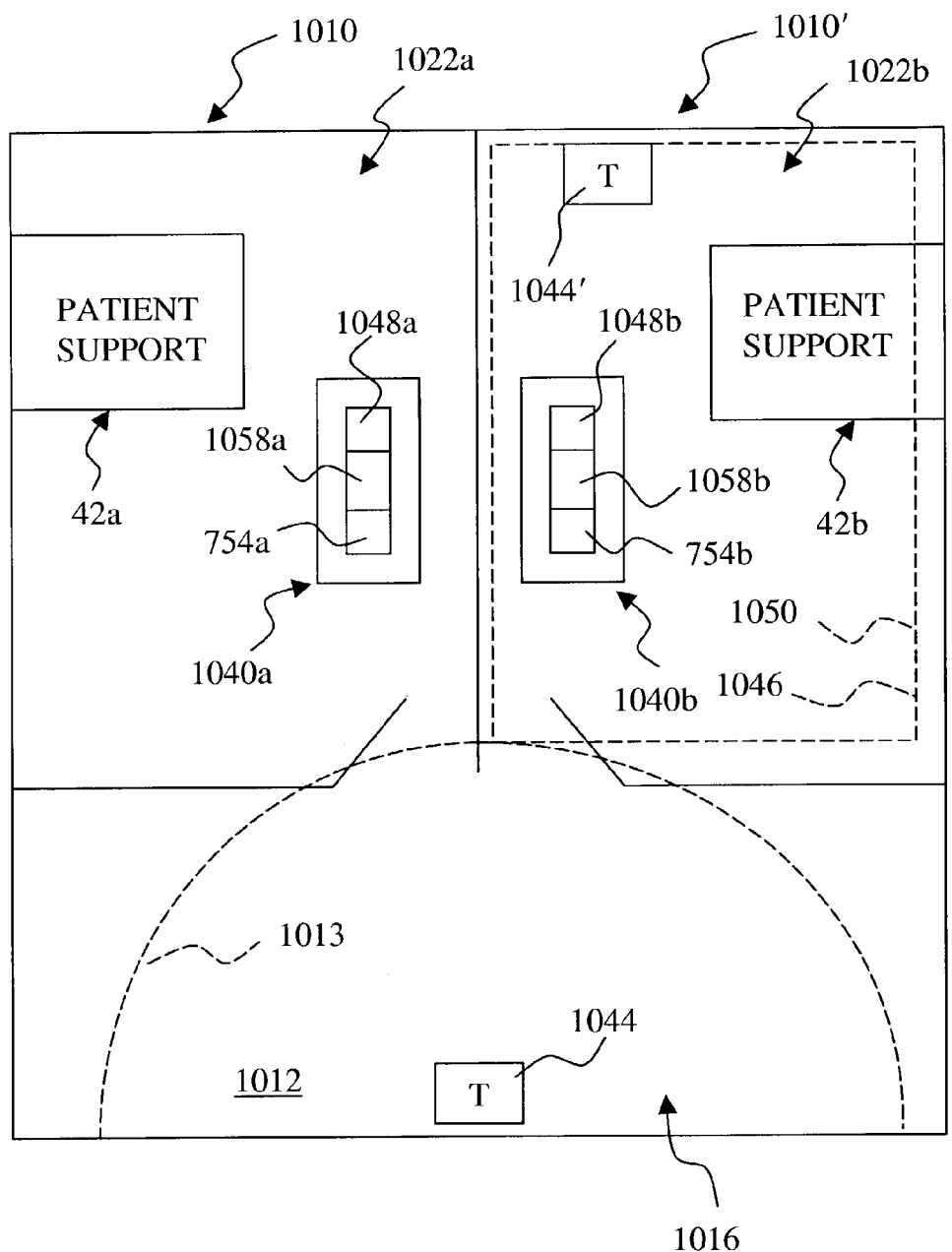
FIG. 46 is a diagrammatical representation of a portion of a healthcare facility incorporating a further illustrative embodiment proximity alarm system.

In yet another illustrative embodiment as shown in FIG. 46, the proximity alarm system 1010 includes an alarm 754*a* coupled to a controller 1040*a*, the alarm 754*a* configured to be activated when the controller 1040*a* is positioned within an undesirable or forbidden area 1012. A transmitter 1044 is positioned in the forbidden area 1012, which is illustrated as a portion of a hallway 1016 outside of the room 1022*a* where the controller 1040*a* is to be kept. The controller 1040*a* includes a receiver 1048*a* coupled to a processor 1058*a* which is coupled to the alarm 754*a*. The receiver 1048*a* is configured to receive a signal transmitted from the transmitter 1044. The signal transmitted from the transmitter 1044 may comprise a radio frequency (RF), infrared (IR), ultrasound or other wireless signal which defines a border or perimeter 1013 of the forbidden area 1012. Upon entering the forbidden area 1012, the receiver 1048*a* receives the signal from the transmitter 1044 and the alarm 754*a* is activated.

Referring further to FIG. 46, in a further illustrative embodiment of the proximity alarm 1010', the transmitter 1044' may be coupled to an antenna 1046 which emits a signal to establish a border or perimeter 1050 enclosing a room 1022*b* where the controller 1040*b* is to be kept. As the controller 1040*b* approaches the perimeter 1050, signals from the antenna 1046 are received by the receiver 1048*b*, which then causes the controller 1040*b* to activate the alarm 754*b*. Additional details of an illustrative proximity alarm 1010' may be found in U.S. Pat. No. 6,111,508, the disclosure of which is expressly incorporated herein by reference.

Figure 47:
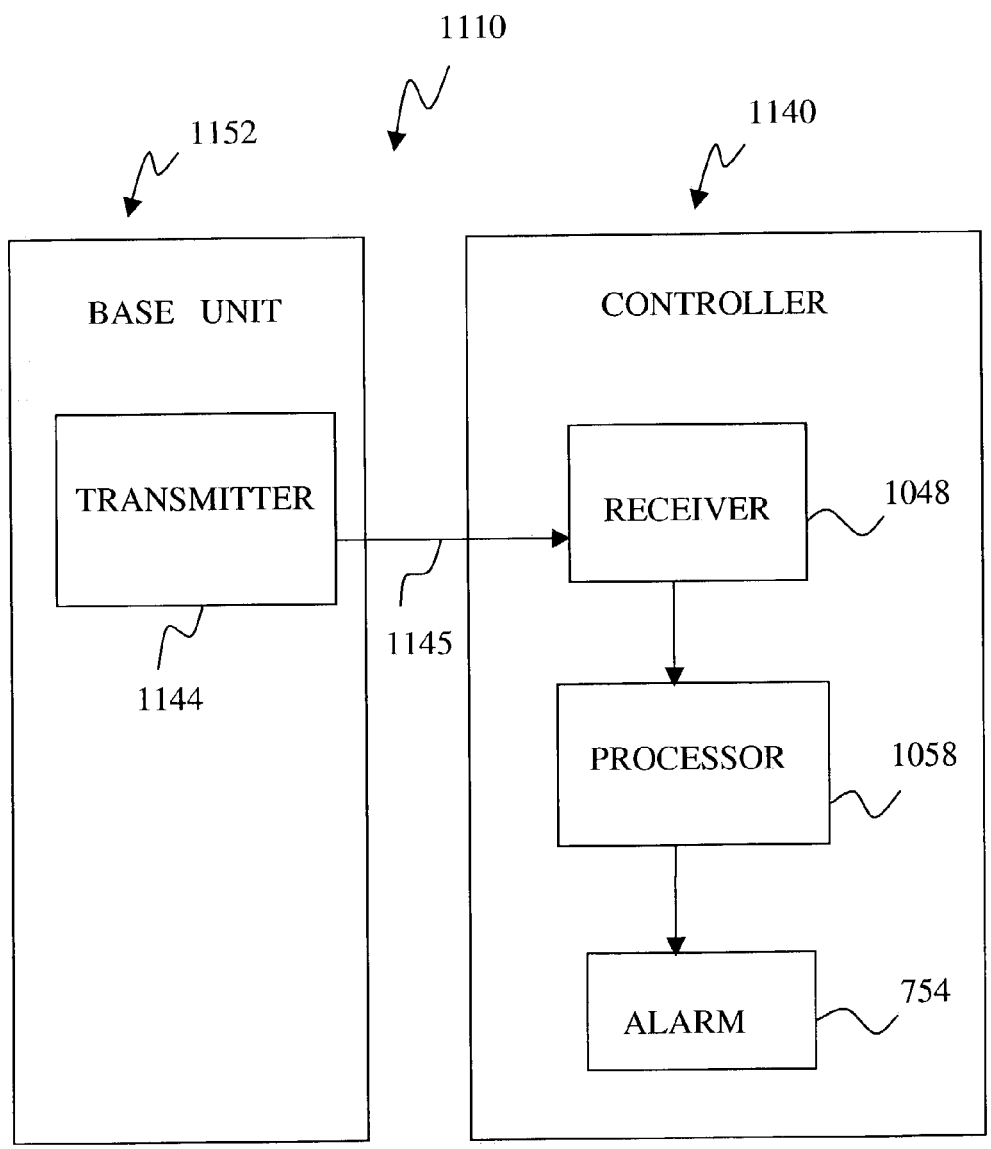
FIG. 47 is a block diagram showing communication between a base unit and a controller of another illustrative embodiment proximity alarm system.

In a further illustrative embodiment as shown in FIG. 47, the proximity alarm system 1110 includes a base unit 1152 having a transmitter 1144, and a controller 1140 having a receiver 1048 configured to receive signals 1145 transmitted by the transmitter 1144. The signals 1145 sent from the transmitter 1144 illustratively comprise low power radio frequency (RF) signals in order to comply with the Federal Communications Commission (FCC) regulations. A processor 1058 is in communication with the receiver 1048 and is configured to activate an alarm 754 when the receiver 1048 receives a signal 1145 from the transmitter 1144 that is below a predetermined threshold strength. It is well-known that the greater the distance between the transmitter 1144 and the receiver 1048, the weaker the signal 1145 will be when received by the receiver 1048. As such, the distance between the base unit 1152 and the controller 1140 may be determined by detecting the signal strength received by the receiver 1048. When the signal strength is below a predetermined value, then the processor 1058 activates the alarm 754. Additional details of an illustrative proximity alarm system 1110 may be found in the U.S. Pat. Nos. 5,614,886, 5,289,163, and 4,871,997, the disclosures of which are expressly incorporated herein by reference.

Figure 48:
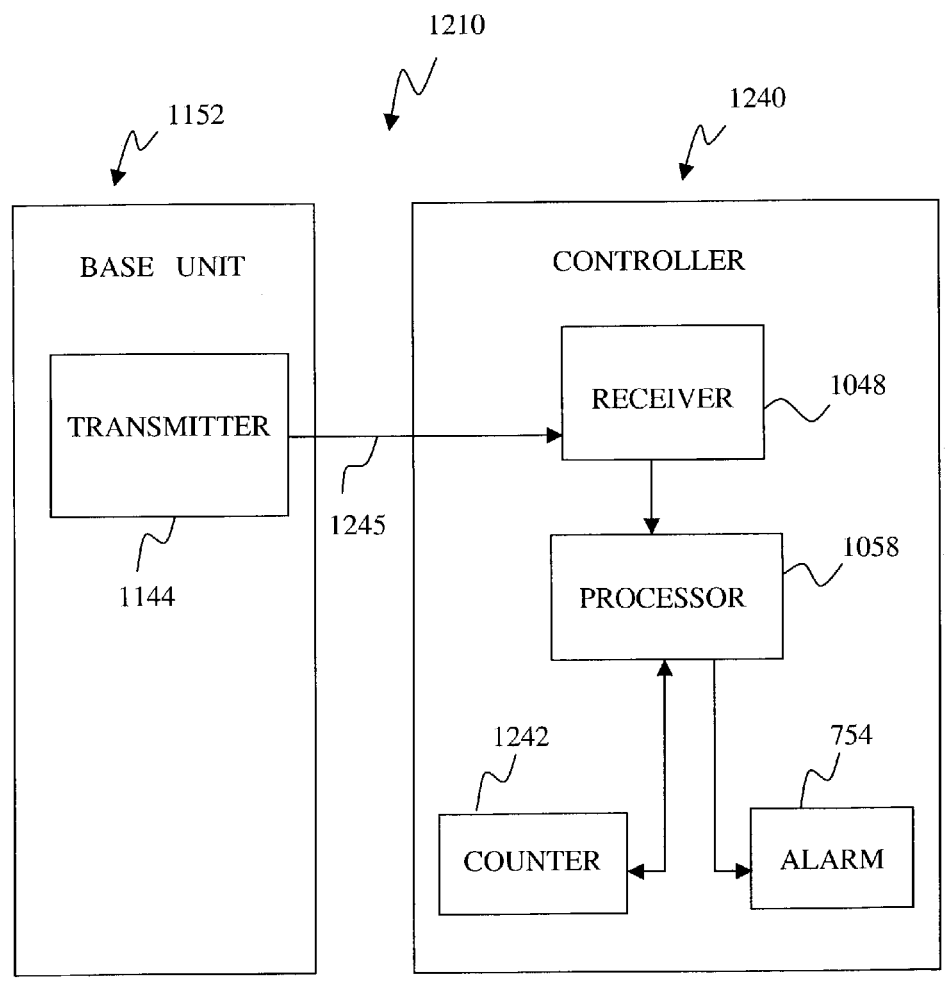
FIG. 48 is a block diagram showing communication between a base unit and a controller of a further illustrative embodiment proximity alarm system.

In another illustrative embodiment as shown in FIG. 48, the proximity alarm system 1210 is configured to activate an alarm 754 when a predetermined time interval expires since communication between a base unit 1152 and a controller 1240. The base unit 1152 includes a transmitter 1144 which sends a short radio frequency (RF) pulse signal 1245 for receipt by a receiver 1048 of the controller 1240. A processor 1058 is in communication with the receiver 1048 and with a counter or clock 1242.

Each time the RF pulse signal 1245 is received by the receiver 1048, the processor 1058 resets the counter 1242. The counter 1242 may be of conventional design and counts or accumulates successive time intervals. If the number of successive time intervals accumulated by the counter 1242 reaches a predetermined value, the processor 1058 activates the alarm 754 to inform a user that the controller 1240 is out of a desired range or is malfunctioning indicating that communication with the base unit 1152 is not possible. The predetermined value for activating the alarm 754 is based upon a desired range of travel of the controller 1240. Upon bringing the controller 1240 back into the desired range, RF pulse signals 1245 from the transmitter 1144 may again be received by the receiver 1048. In response, the processor 1058 resets the counter 1242, typically to a value of zero. Additional details of the proximity alarm system 1210 may be found in U.S. Pat. Nos. 4,908,627 and 5,722,059, the disclosures of which are expressly incorporated herein by reference.

The preceding embodiments of the proximity alarm system provide that the proximity alarms 754 may be located within the controller 740, 1040, 1140, 1240 within the base unit 752, 1152 coupled to the patient support 42, or in another location remote both from the controller and the base unit. The alarm 754 positioned remote from the controller 740, 1040, 1140, 1240 may be desirable in a multi-patient support environment where it could be difficult to associate a controller with a particular device/patient support 42. The alarm 754 within the base unit 752, 1152 attached to the device/patient support 42 will thereby communicate to the user which device/patient support 42 is associated with the displaced controller 740, 1040, 1140, 1240. Also, embodiments are envisioned where the controller 740, 1040, 1140, 1240 can be switched to a tracking mode where the controller tracks the base unit 752, 1152 to tell the user where the base unit is located. A controller 740, 1040, 1140, 1240 with a tracking mode is described in U.S. Pat. No. 5,650,769, the disclosure of which is expressly incorporated herein by reference.

Additional features may be common to all embodiments of the proximity alarm system. One such feature is a controller call button illustratively coupled to the device/patient support 42. Pressing the button activates a signal device, illustratively the alarm 754, within the controller 740, 1040, 1140, 1240 thereby assisting the user in locating the controller. Another common feature may be a controller release button. The controller release button disables the proximity alarm system 710 thereby allowing the controller 740, 1040, 1140, 1240 to extend beyond the normal boundaries without the alarm 754 sounding. Such a feature is desirable when the controller 740, 1040, 1140, 1240 must be removed from the room in instances such as repair or software/hardware updating. An alarm system with a controller release button is disclosed in U.S. Pat. No. 6,304,186, the disclosure of which is expressly incorporated herein by reference. Another illustrative feature which may be common throughout the embodiments is the use of an exclusively matched controller 740, 1040, 1140, 1240 and base unit 752, 1152. The controller 740, 1040, 1140, 1240 is configured such that the controller only communicates with the corresponding base unit 752, 1152. This is done to prevent cross-talk between nearby controllers 740, 1040, 1140, 1240 and base units 752, 1152. This may be accomplished through the use of access code headers transmitted with the signal, by the use of different transmission waveforms, or otherwise.

A controller according to the present invention thus provides a single, hand-held control unit that can operate multiple medical devices, such as both a surgical table and a mattress system. The controller permits both wireless operation or a conventional cable system. A display is provided, such as a relatively large, backlit display, that is easy to see and understand, and provides a friendly user-interface without using small buttons. Touch-screen display 116 preferably is flat, easy to clean, and durable. The controller provides a menu driven system that effectively displays to a user the information necessary for any given adjustment of a controlled system, thus optimizing the ease and effectiveness of its use. The use of named, predefined configurations, such as for surgical table 42 in automatic adjustment menus 132, 232, allows for personalized care giver and procedure names, as well as for "single button set-up" of a complex system. Integrated help, operating, and servicing displays further enhance the ease of use and utility of a controller according to the present invention.

Although the invention has been described in detail with reference to certain preferred embodiments, variations and modifications exist within the scope and spirit of the present invention as described and defined in the following claims.

What is claimed is:

1. A medical device controller apparatus comprising:
   a portable housing;
   a user input device coupled to the housing; and
   a processor coupled to the housing, the processor being configured to command a controllable medical device, to determine if a predetermined distance from a base unit is exceeded, and to signal an alert if the predetermined distance from the base unit is exceeded,
   and a display coupled to the processor, wherein the patient support apparatus further comprises a mattress located on the frame to support a patient, the mattress being adjustable to a plurality of different mattress configurations for the plurality of different medical procedures, and wherein the processor is configured to provide a menu on the display of a plurality of defined configurations of the frame and mattress, the processor being configured to command the frame and mattress to move to a selected one of the plurality of predefined configurations based on a user input.

2. The apparatus of claim 1, further comprising a display coupled to the housing.

3. The apparatus of claim 1, wherein the alert is at least one of an audible alarm, a visual alarm, and a vibratory alarm.

4. The apparatus of claim 1, wherein the alert is at least one of a personal computer and a pager.

5. The apparatus of claim 1, wherein the controllable medical device is a patient support apparatus comprising a base, and a frame coupled to the base, the frame including a plurality of frame sections movable relative to each other to position the frame in a plurality different frame configurations for a plurality of different medical procedures.

6. The apparatus of claim 1, wherein the processor is further configured to command a temperature control system.

7. The apparatus of claim 1, wherein the processor is further configured to command a lighting system.

8. The apparatus of claim 1, wherein the user input device includes a first switch configured to select one of the frame sections, and a second switch configured to adjust the frame section selected by the first switch.

9. The apparatus of claim 1, wherein the controllable medical device is an operating room system comprising an articulated frame having a plurality of segments, a frame controller coupled to the frame to move at least one of the segments, a mattress having at least one chamber, a mattress controller coupled to the to control an amount of fluid in the at least one chamber; and a user interface controller.

10. The apparatus of claim 9, wherein the controllable medical device further comprises a lighting system having at least one light head, a lighting controller coupled to the lighting system to control an intensity of light from the at least one light head, and the user interface controller is configured to send control signals to the table controller and to the lighting controller.

11. The apparatus of claim 9, further comprises a patient thermal regulation system, a thermal regulation controller coupled to the patient thermal regulation system, and the user interface controller is configured to send control signals to the table controller and to the thermal regulation controller.

12. The apparatus of claim 1, further comprising a first transmitter and a first receiver both coupled to one of the base unit and the housing, a second transmitter and second receiver both coupled to the other of the housing and the base unit, the first transmitter being configured to transmit a first signal to the second receiver and the second transmitter being configured to transmit a second signal to the first receiver in response to the second receiver receiving the first signal, and a processor in communication with the first transmitter and the first receiver.

13. The apparatus of claim 12, wherein the processor is configured to signal the alert when the time between the first transmitter transmitting the first signal and the first receiver receiving the second signal is greater than a predetermined value.

14. The apparatus of claim 1, further comprising a first tag coupled to the base unit, a second tag couple to the housing, and a monitor configured to receive first and second signals transmitted by the first and second tags.

15. The apparatus of claim 14, wherein the first tag and the second tag comprise RFID tags, and the monitor comprises an RFID detector.

16. The apparatus of claim 14, further comprising a processor which electronically links the first tag to the second tag and signals the alert when the monitor indicates that the first tag and the second tag are separated by a distance greater than a predetermined value.

17. The apparatus of claim 14, further comprising a plurality of monitors defining a plurality of different detection zones, and a processor in communication with the plurality of monitors and configured to signal the alert when the first tag is detected within a first detection zone and the second tag is detected within a second detection zone.

18. The apparatus of claim 1, further comprising one of a receiver and a transmitter coupled to the housing, the other of the transmitter and the receiver located in restricted zone, the transmitter being configured to transmit a signal which is configured to be received by the receiver, and a processor in communication with the receiver and configured to signal the alert when the signal from the transmitter is received by the receiver.

19. The apparatus of claim 18, wherein the other of the transmitter and the receiver establishes a perimeter defining the restricted zone.

20. The apparatus of claim 1, further comprising a transmitter coupled to one of the housing and the base unit, a receiver coupled to the other of the base unit and the housing, the transmitter being configured to transmit a signal to the receiver, and a processor configured to determine a strength of the signal received by the receiver and to signal the alert when the strength is below a predetermined value.

21. The apparatus of claim 1, further comprising a transmitter coupled to one of the housing and the tag base unit, a receiver coupled to the other of the base unit and the housing, the transmitter being configured a signal to the receiver, a counter configured to count successive time intervals between transmission of the signal from the transmitter and receipt of the signal by the receiver, and a processor configured to signal the alert when the count from the counter exceeds a predetermined value.

22. The apparatus of claim 1, wherein the processor is configured to track the location of the base unit and provide an indication on a display of the location of the base unit.

23. The apparatus of claim 1, wherein the base unit includes a controller call button configured to signal the alert on the housing.

24. The apparatus of claim 1, further comprising a controller release button in communication with the processor wherein activation of the controller release button causes the processor not to signal the alert when the predetermined distance from the base unit is exceeded.

25. A control system configured to control the operation of a device in a healthcare facility, the control system comprising:
a controllable device;
a controller in communication with the controllable device and including a portable housing;
a user input device coupled to the housing;
a tag coupled to the housing;
a monitor located in a restricted zone, the monitor being configured to transmit an excitation signal for receipt by the tag; and
a processor in communication with the monitor and configured to signal an alert when the excitation signal is received by the tag,
and a display coupled to the processor, wherein the patient support apparatus further comprises a mattress located on the frame to support a patient, the mattress being adjustable to a plurality of different mattress configurations for the plurality of different medical procedures, and wherein the processor is configured to provide a menu on the display of a plurality of defined configurations of the frame and mattress, the processor being configured to command the frame and mattress to move to a selected one of the plurality of predefined configurations based on a user input.

26. The system of claim 25, wherein the other of the transmitter and the receiver establishes a perimeter defining the restricted zone.

27. The system of claim 25, wherein the other of the transmitter and the receiver is positioned at a room exit.

28. The system of claim 25, wherein the tag is configured to transmit a response signal in response to receiving the excitation signal, the monitor is configured to receive the response signal, and the monitor is configured to transmit a signal to the processor in response to receiving the response signal thereby instructing the processor to signal the alert.

29. A medical device control system comprising:
a controllable medical device;
a controller in communication with the controllable medical device and including a portable housing;
a transmitter coupled to one of the housing and the base unit;
a receiver coupled to the other of the base unit and the housing, the transmitter being configured to transmit a signal to the receiver; and
a processor configured to determined a strength to the signal and to signal an alert when the strength is below a predetermined value,
and a display coupled to the processor, wherein the patient support apparatus further comprises a mattress located on the frame to support a patient, the mattress being adjustable to a plurality of different mattress configurations for the plurality of different medical procedures, and wherein the processor is configured to provide a menu on the display of a plurality of defined configurations of the frame and mattress, the processor being configured to command the frame and mattress to move to a selected one of the plurality of predefined configurations based on a user input.

30. A medical device control system comprising:
a controllable medical device;
a first transmitter associated with the controllable medical device and configured to transmit a first signal;
a first receiver associated with the controllable medical device;

a processor in communication with the first transmitter and the first receiver;

a controller including a portable housing;

a second transmitter coupled to the housing and configured to transmit a second signal for receipt by the first receiver;

a second receiver coupled to the housing and configured to receive the first signal from the first transmitter, the second transmitter configured to transmit the second signal in response to the second receiver receiving the first signal; and a user input device supported by the housing and in communication with the processor;

wherein the processor is configured to command the controllable medical device, to determine if a predetermined time between the first transmitter transmitting the first signal and the first receiver receiving the second signal is exceeded, and to signal an alert if the processor determines the predetermined time is exceeded, and and a display coupled to the processor, wherein the patient support apparatus further comprises a mattress located on the frame to support a patient, the mattress being adjustable to a plurality of different mattress configurations for the plurality to different medical procedures, and wherein the processor is configured to provide a menu on the display of a plurality of defined configurations of the frame and mattress, the processor being configured to command the frame and mattress to move to a selected one of the plurality of predefined configurations based on a user input.

* * * * *